United States Patent
Kobayashi et al.

(10) Patent No.: US 10,302,944 B2
(45) Date of Patent: May 28, 2019

(54) HEAD-MOUNT TYPE DISPLAY DEVICE AND METHOD OF CONTROLLING HEAD-MOUNT TYPE DISPLAY DEVICE

(71) Applicant: Seiko Epson Corporation, Tokyo (JP)

(72) Inventors: Shinichi Kobayashi, Azumino (JP); Toshikazu Uchiyama, Chino (JP); Hitomi Wakamiya, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 112 days.

(21) Appl. No.: 14/314,835

(22) Filed: Jun. 25, 2014

(65) Prior Publication Data
US 2015/0002373 A1 Jan. 1, 2015

(30) Foreign Application Priority Data
Jun. 28, 2013 (JP) ................................. 2013-136054
Mar. 17, 2014 (JP) ................................. 2014-053187

(51) Int. Cl.
G02B 27/00 (2006.01)
G02B 27/01 (2006.01)
A61B 5/024 (2006.01)

(52) U.S. Cl.
CPC ........ G02B 27/017 (2013.01); A61B 5/02416 (2013.01); A61B 5/02438 (2013.01);
(Continued)

(58) Field of Classification Search
CPC ...... G02B 27/0093; G02B 27/01; G06T 7/00; G06T 11/00; G06T 19/006;
(Continued)

(56) References Cited

U.S. PATENT DOCUMENTS

| | | | | |
|---|---|---|---|---|
| 3,946,725 A | * | 3/1976 | Bolshov | A61B 5/0245 600/519 |
| 5,406,952 A | * | 4/1995 | Barnes | A61B 5/021 600/485 |

(Continued)

FOREIGN PATENT DOCUMENTS

| | | |
|---|---|---|
| JP | 07-255669 A | 10/1995 |
| JP | 07-287187 A | 10/1995 |

(Continued)

OTHER PUBLICATIONS

Ministry of Internal Affairs and Communications, "Report on Government-funded Research and Study Regarding the Effects of Content on a Living Body," Mar. 2004, pp. 1-3.

(Continued)

*Primary Examiner* — Temesghen Ghebretinsae
*Assistant Examiner* — Paras D Karki
(74) *Attorney, Agent, or Firm* — ALG Intellectual Property, LLC

(57) ABSTRACT

A head-mount type display device includes an image display device adapted to allow a user to visually recognize an image in a state of being mounted on a head of a user, a detection section disposed in the image display device and adapted to detect biological information of the user, a control section adapted to perform control of the image visually recognized by the user using the image display device, and an annunciation section adapted to inform the user of image control information as information related to the control of the image based on a variation in the biological information detected.

10 Claims, 14 Drawing Sheets

(52) U.S. Cl.
 CPC .......... *G02B 27/0093* (2013.01); *G02B 27/00* (2013.01); *G02B 27/01* (2013.01); *G02B 2027/014* (2013.01); *G02B 2027/0178* (2013.01)

(58) Field of Classification Search
 CPC . G06T 19/0468; G06T 3/113; H04N 13/0468; A61B 3/113; A61B 5/0006; A61B 5/04; G06F 3/015; G06F 3/011; G06K 9/00597; A61F 2/72
 See application file for complete search history.

(56) References Cited

U.S. PATENT DOCUMENTS

| | | | |
|---|---|---|---|
| 9,264,803 B1* | 2/2016 | Johnson | H04R 3/00 |
| 2005/0080347 A1* | 4/2005 | Sheth | A61B 5/046 |
| | | | 600/515 |
| 2008/0062291 A1* | 3/2008 | Sako et al. | 348/294 |
| 2009/0198145 A1* | 8/2009 | Chow | 600/544 |
| 2010/0013739 A1 | 1/2010 | Sako et al. | |
| 2011/0050428 A1* | 3/2011 | Istoc | 340/573.1 |
| 2011/0082378 A1* | 4/2011 | Messier | A61B 5/0002 |
| | | | 600/509 |
| 2011/0190646 A1* | 8/2011 | Kato | A61B 5/02455 |
| | | | 600/500 |
| 2012/0095520 A1* | 4/2012 | Zhang | A61B 5/0422 |
| | | | 607/15 |
| 2013/0009868 A1 | 1/2013 | Sako et al. | |
| 2014/0292637 A1* | 10/2014 | Peng et al. | 345/156 |
| 2014/0306703 A1* | 10/2014 | Shirai | G01R 33/56518 |
| | | | 324/309 |
| 2014/0375559 A1 | 12/2014 | Sako et al. | |
| 2016/0124503 A1 | 5/2016 | Sako et al. | |

FOREIGN PATENT DOCUMENTS

| | | |
|---|---|---|
| JP | 09-149339 A | 6/1997 |
| JP | 11-237581 A | 8/1999 |
| JP | H11-299734 A | 11/1999 |
| JP | 2002-125137 A | 4/2002 |
| JP | 2004-236187 A | 8/2004 |
| JP | 2006-158479 A | 6/2006 |
| JP | 2011-120824 A | 6/2011 |
| JP | 2013-077013 A | 4/2013 |
| JP | 2013-114123 A | 6/2013 |
| JP | 2013-176535 A | 9/2013 |

OTHER PUBLICATIONS

NHK & The Japan Commercial Broadcasters Association, "Guideline regarding Video Effect Techniques used in Animation and the Like," Apr. 1, 2006, pp. 1-3.

* cited by examiner

HEAD-MOUNT TYPE DISPLAY DEVICE AND METHOD OF CONTROLLING HEAD-MOUNT TYPE DISPLAY DEVICE

BACKGROUND

1. Technical Field

The present invention relates to a head-mount type display device.

2. Related Art

There has been known ahead-mount type display device (a head-mounted display (HMD)) as a display device to be used in the state of being mounted on the head. The head-mount type display device generates image light representing an image using, for example, a liquid crystal display and a light source, and then guides the image light thus generated to the eyes of the user using a projection optical system and a light guide plate to thereby make the user visually recognize a virtual image.

JP-A-2002-125137 (Document 1) discloses a device capable of operating the head-mount type display device by remote control. When a predetermined time has elapsed from when the head-mount type display device is powered ON, this device displays a message representing the fact that the head-mount type display device has been used for a long period of time to thereby call attention to the user in using the head-mount type display device.

Further, JP-A-2013-176535 (Document 2) discloses a technology capable of measuring the pulse wave while reducing an influence of a noise on a measurement signal by analyzing the fluctuation in the respective measurement signals detected by a plurality of light receiving sections in a pulse wave measurement device to be mounted on the wrist.

Further, as examples of related art documents, there can be cited the research study report on an influence of contents on a living body (March 2004, Ministry of Internal Affairs and Communications), and the guideline on an imaging technique such as animation (2006, Japan Broadcasting Corporation, The Japan Commercial Broadcasters Association).

However, in the technology described in Document 1, the control for avoiding prolonged use, such as display of a warning message or forced stop of the head-mount type display device is performed without exception when a predetermined time has elapsed regardless of the type of the content to be visually recognized by the user or the health condition of the user. Since in the related art technology, the control for avoiding prolonged use is performed without exception after the predetermined time has elapsed as described above, there is a problem that in some cases, the timing of such control is too early, or by contraries too late depending on the physical condition of the user or the individual difference between the users. It should be noted that such a problem exists not only in the control for avoiding prolonged use, but also in other control such as the control of the luminance of the image light in a similar manner.

Further, in the technology described in Document 2, although the pulse wave of the user can more accurately be detected than ever, there is a demand for using the pulse wave thus detected in controlling a variety of types of devices. Further, there is a problem that the biological information of the user other than the pulse wave also needs to be detected.

SUMMARY

An advantage of some aspects of the invention is to solve at least a part of the problems described above, and the invention can be implemented as the following aspects.

(1) An aspect of the invention provides a head-mount type display device. The head-mount type display device includes an image display device adapted to allow a user to visually recognize an image in a state of being mounted on a head of a user, a detection section adapted to detect biological information of the user, and then transmit the biological information to the image display device, a control section adapted to perform control of the image visually recognized by the user using the image display device, and an annunciation section adapted to inform the user of image control information as information related to the control of the image based on a variation in the biological information detected. According to the head-mount type display device of this aspect of the invention, since the control of the display image to be visually recognized by the user is performed in accordance with the individual difference between the users based on the malfunction of the automatic nervous system detected in the individual user, convenience of the user can be enhanced. Further, by decreasing the luminance of the image light, it is possible to reduce the load of the user to thereby restore the automatic nervous system to the normal state.

(2) In the head-mount type display device according to the aspect of the invention, the detection section may be disposed so as to have contact with the user, and keep the contact with the user. According to the head-mount type display device of this aspect of the invention, the biological information of the user can more easily be detected in more detail, and the control corresponding to the biological information of the user is easy to perform.

(3) In the head-mount type display device according to the aspect of the invention, the biological information may be information for identifying a pulse wave. According to the head-mount type display device of this aspect of the invention, the variation in the automatic nervous system of the user can easily be detected, and thus, the convenience of the user can further be enhanced. Further, since no large-size equipment is required for detecting the variation in the automatic nervous system of the user, the convenience of the user can be enhanced while inhibiting the portability of the image display device from degrading.

(4) In the head-mount type display device according to the aspect of the invention, the annunciation section may inform the user of the image control information based on a variation in heartbeat fluctuation due to the pulse wave. According to the head-mount type display device of this aspect of the invention, the variation in the automatic nervous system of the user can easily be detected, and thus, the convenience of the user can further be enhanced. Further, since no large-size equipment is required for detecting the variation in the automatic nervous system of the user, the convenience of the user can be enhanced while inhibiting the portability of the image display device from degrading.

(5) In the head-mount type display device according to the aspect of the invention, the biological information may be information for identifying an open-close state of an eye. According to the head-mount type display device of this aspect of the invention, since the control of the display image to be visually recognized is performed in accordance with the individual difference between the users based on the malfunction of the automatic nervous system detected in the individual user, the convenience of the user can be enhanced.

(6) In the head-mount type display device according to the aspect of the invention, the biological information may be information for identifying a state of a pupil of the user. According to the head-mount type display device of this aspect of the invention, since the control of the display image to be visually recognized is performed in accordance with the individual difference between the users based on the malfunction of the automatic nervous system detected in the individual user, the convenience of the user can be enhanced.

(7) The head-mount type display device according to the aspect of the invention, the biological information may be information for identifying redness of an eye. According to the head-mount type display device of this aspect of the invention, since the degree of the devotion to the image to be visually recognized by the user and the viewing time are estimated by determining the degree of the redness of the eyes of the user, and the control of the image light is performed based on the variation in physical condition detected in the individual user, the convenience of the user can be enhanced.

(8) In the head-mount type display device according to the aspect of the invention, the biological information may be information for identifying at least one of a state of an external ocular muscle and a state of an internal ocular muscle. According to the head-mount type display device of this aspect of the invention, since the fatigue accumulated in the external ocular muscle or the internal ocular muscle of the user is determined, and the control of the image light is performed in accordance with the fatigue of the eyes corresponding to the individual difference between the users, the convenience of the user can be enhanced.

(9) In the head-mount type display device according to the aspect of the invention, the biological information may be information for identifying a body temperature. According to the head-mount type display device of this aspect of the invention, since the control of the display image is performed in accordance with the variation in the body temperature of the individual user, the convenience of the user can be enhanced.

(10) In the head-mount type display device according to the aspect of the invention, the biological information may be information for identifying perspiration. According to the head-mount type display device of this aspect of the invention, since the control of the image light is performed in accordance with the perspiration state of the individual user, the convenience of the user can be enhanced.

(11) In the head-mount type display device according to the aspect of the invention, the annunciation section may make the control section perform control of making the user visually recognize the image control information as an image using the image display device. According to the head-mount type display device of this aspect of the invention, it is easy for the user to recognize the image control information, and thus the convenience of the user can further be enhanced.

(12) In the head-mount type display device according to the aspect of the invention, the annunciation section may output the image control information as a sound to make the user recognize the image control information. According to the head-mount type display device of this aspect of the invention, since it is possible to call attention to the user while preventing the display image presently viewed by the user from being interfered, the convenience of the user can be enhanced.

(13) In the head-mount type display device according to the aspect of the invention, the control of the image may be control of changing the image so as not to be visually recognized by the user. According to the head-mount type display device of this aspect of the invention, since the image to be visually recognized by the user is terminated to achieve restoration of the health condition of the user in the case in which the malfunction of the automatic nervous system of the user, physical deconditioning of the user, or the like is detected, the convenience of the user can further be enhanced.

All of the constituents provided to each of the aspects of the invention described above are not necessarily essential, and in order to solve all or a part of the problems described above, or in order to achieve all or a part of the advantages described in the specification, it is possible to arbitrarily make modification, elimination, replacement with another new constituent, partial deletion of restriction content on some of the constituents. Further, in order to solve all or apart of the problems described above, or in order to achieve all or a part of the advantages described in the specification, it is also possible to combine some or all of the technical features included in one of the aspects of the invention with some or all of the technical features included in another of the aspects of the invention to thereby form an independent aspect of the invention.

For example, an aspect of the invention can be implemented as a device provided with at least one or all of the four elements, namely the image display device, the detection section, the control section, and the annunciation section. In other words, it is also possible for the image display device to be included or not to be included in the device. Further, it is also possible for the detection section to be included or not to be included in the device. Further, it is also possible for the control section to be included or not to be included in the device. Further, it is also possible for the annunciation section to be included or not to be included in the device. It is also possible for the image display device to make the user visually recognize the image in a state of being mounted on the head of the user. It is also possible for the detection section to be disposed in, for example, the image display device, and detect the biological information of the user. It is also possible for the control section to perform the control of the image. It is also possible for the annunciation section to inform the user of image control information as information related to the control of the image based on a variation in the biological information detected. Such a device can be implemented as, for example, a head-mount type display device, but can also be implemented as a device other than the head-mount type display device. According to such an aspect of the invention, it is possible to solve at least one of a variety of problems such as improvement in operability and simplification of the device, integration of the device, and enhancement of convenience of the user using the device. Some or all of the technical features of the head-mount type display device described above as each of the aspects of the invention can be applied to this device.

The invention can be implemented in various forms other than the head-mount type display device. The invention can be implemented in the forms such as a method of controlling a head-mount type display device, a head-mount type display system, a computer program for implementing the function of the head-mount type display system, a recording medium on which the computer program is recorded, and a data signal including the computer program and embodied in a carrier wave.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
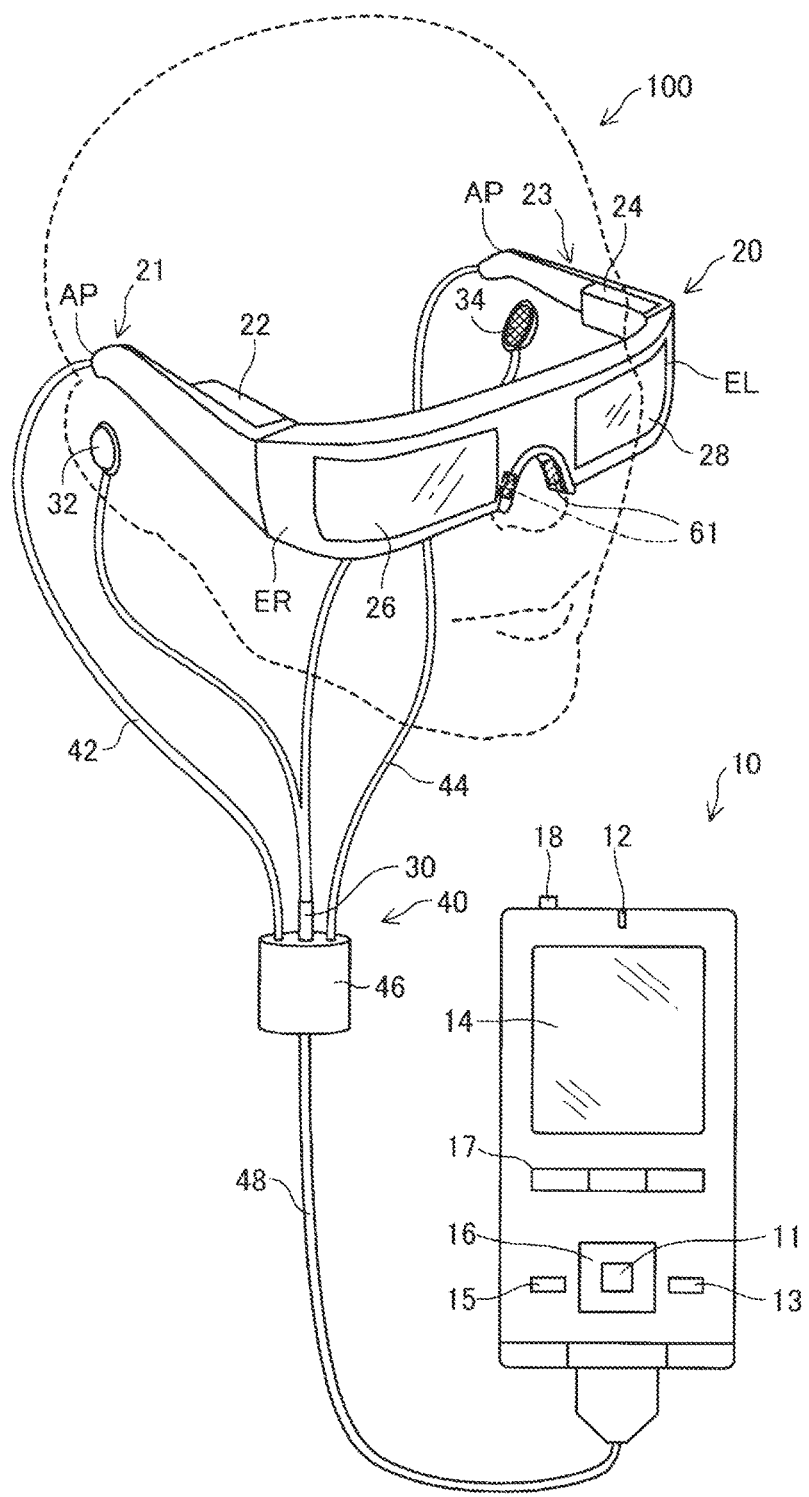
FIG. 1 is an explanatory diagram showing an exterior configuration of a head-mount type display device.

Then, some embodiments of the invention will be explained in the following order based on specific examples.
A. First Embodiment
A-1. Configuration of Head-Mount Type Display Device
A-2. Relationship Between Pulse Wave and Automatic Nervous System
A-3. Display Control Process
B. Second Embodiment
C. Modified Examples A. First Embodiment A-1. Configuration of Head-Mount Type Display Device FIG. 1 is an explanatory diagram showing an exterior configuration of a head-mount type display device 100. The head-mount type display device 100 is a display device to be mounted on the head, and is also called a head mounted display (HMD). The head-mount type display device 100 according to the first embodiment is an optical transmissive head-mount type display device allowing the user to visually recognize a virtual image and at the same time visually recognize an external sight directly. It should be noted that in the present specification, the virtual image to be visually recognized by the user using the head-mount type display device 100 is also referred to as a "display image" for the sake of convenience. Further, emission of the image light generated based on the image data is also referred to as "display of the image."

The head-mount type display device 100 is provided with an image display section 20 for making the user visually recognize the virtual image in the state of being mounted on the head of the user, and a control section 10 (a controller 10) for controlling the image display section 20.

The image display section 20 is a wearable body to be mounted on the head of the user, and has a shape of a pair of glasses in the first embodiment. The image display section 20 includes a right holding section 21, a right display drive section 22, a left holding section 23, a left display drive section 24, a right optical image display section 26, a left optical image display section 28, and a pulse wave sensor 61. It should be noted that the image display section 20 corresponds to an image display device in the appended claims. The right optical image display section 26 and the left optical image display section 28 are disposed so as to be located in front of the right and left eyes of the user, respectively, when the user wears the image display section 20. One end of the right optical image display section 26 and one end of the left optical image display section 28 are connected to each other at a position corresponding to the glabella of the user when the user wears the image display section 20.

The right holding section 21 is a member disposed so as to extend from an end portion ER, which is the other end of the right optical image display section 26, to a temporal region of the head of the user when the user wears the image display section 20. Similarly, the left holding section 23 is a member disposed so as to extend from an end portion EL, which is the other end of the left optical image display section 28, to a temporal region of the head of the user when the user wears the image display section 20. The right holding section 21 and the left holding section 23 hold the image display section 20 in the head of the user in such a manner as the temples of the pair of glasses.

The right display drive section 22 and the left display drive section 24 are disposed on the sides to be opposed to the head of the user when the user wears the image display section 20. It should be noted that hereinafter the right holding section 21 and the left holding section 23 are collectively referred to simply as "holding sections," the right display drive section 22 and the left display drive section 24 are collectively referred to simply as "display drive sections," and the right optical image display section 26 and the left optical image display section 28 are collectively referred to simply as "optical image display sections."

The display drive sections 22, 24 include liquid crystal displays 241, 242 (hereinafter also referred to as "LCDs 241, 242"), projection optical systems 251, 252, and so on (see FIG. 3). The details of the configuration of the display drive sections 22, 24 will be described later. The optical image display sections 26, 28 as optical members include light guide plates 261, 262 (see FIG. 2), and a light control plate. The light guide plates 261, 262 are each formed of a light transmissive resin material or the like, and guide the image light output from the display drive sections 22, 24 to the eyes of the user. The light control plate is a thin-plate like optical element, and is disposed so as to cover the obverse side of the image display section 20, which is the side opposite to the side of the eyes of the user. The light control plate protects the light guide plates 261, 262 to suppress damages, adhesion of dirt, and so on to the light guide plates 261, 262. Further, by controlling the light transmittance of the light control plate, an amount of the outside light entering the eyes of the user is controlled, and thus, the easiness of the visual recognition of the virtual image can be controlled. It should be noted that the light control plate can be eliminated.

The pulse wave sensor 61 is a sensor for detecting the pulse wave of the user as the wearer of the image display section 20. The pulse wave sensor 61 is a contactless sensor disposed on the user side in the image display section 20 in the state in which the image display section 20 is mounted on the head of the user. The pulse wave sensor 61 emits light toward the inside of the living body (e.g., a nose) of the user with a light emitting diode, and then receives the reflected light corresponding to the passage of blood varying in accordance with the heartbeat in the living body. Since hemoglobin included in the blood has a strong absorption spectrum to the light in a certain wavelength band, the reflected light thus received varies in accordance with the variation in the volume (a blood flow rate) of the blood flowing through a blood vessel. By converting the reflected light into an electric signal and then detecting the electric signal, the voltage value representing the blood flow rate is obtained to obtain the waveform of the pulse wave of the user.

The image display section 20 further includes a connection section 40 for connecting the image display section 20 to the control section 10. The connection section 40 includes a main body cord 48 to be connected to the control section 10, a right cord 42, a left cord 44, and a connecting member 46. The right cord 42 and the left cord 44 are obtained by branching the main body cord 48 into two cords. The right cord 42 is inserted into the housing of the right holding section 21 from a tip portion AP in the extending direction of the right holding section 21, and is connected to the right display drive section 22. Similarly, the left cord 44 is inserted into the housing of the left holding section 23 from a tip portion AP in the extending direction of the left holding section 23, and is connected to the left display drive section 24. The connecting member 46 is disposed at a branch point of the main body cord 48 and the right cord 42 and the left cord 44, and includes a jack to which an earphone plug 30 is connected. A right earphone 32 and a left earphone 34 extend from the earphone plug 30.

The image display section 20 and the control section 10 perform transmission of various signals via the connection section 40. Connectors (not shown) to be fitted with each other are provided to an end portion of the main body cord 48 on the opposite side to the connecting member 46 and the control section 10, respectively. The control section 10 and the image display section 20 are connected to each other or separated from each other in accordance with fitting/releasing of the connector of the main body cord 48 and the connector of the control section 10. As the right cord 42, the left cord 44, and the main body cord 48, there are adopted, for example, metal cables or optical fibers.

The control section 10 is a device for controlling the head-mount type display device 100. The control section 10 includes a determination key 11, a lighting section 12, a display switching key 13, a track pad 14, a luminance switching key 15, direction keys 16, a menu key 17, and a power switch 18. The determination key 11 detects a holding-down operation, and then outputs a signal used in the control section 10 for determining the content of the operation. The lighting section 12 gives notice of the operation state of the head-mount type display device 100 with the lighting state of the lighting section 12. As the operation state of the head-mount type display device 100, there can be cited, for example, an ON/OFF state of the power. As the lighting section 12, there is used, for example, a light emitting diode (LED). The display switching key 13 detects a holding-down operation, and then outputs, for example, a signal for switching the display mode of the content moving image between a 3D mode and a 2D mode. The track pad 14 detects the finger operation of the user on the operation surface of the track pad 14, and then outputs a signal corresponding to the detection content. As the track pad 14, a variety of types of track pad are adopted such as an electrostatic track pad, a pressure-detection track pad, or an optical track pad. The luminance switching key 15 detects a holding-down operation, and then outputs a signal for increasing or decreasing the luminance of the image display section 20. The direction keys 16 detect a holding-down operation to the keys corresponding to up, down, right, and left directions, and then output a signal corresponding to the detection content. The power switch 18 detects a sliding operation of the switch to thereby switch the powering state of the head-mount type display device 100.

Figure 2:
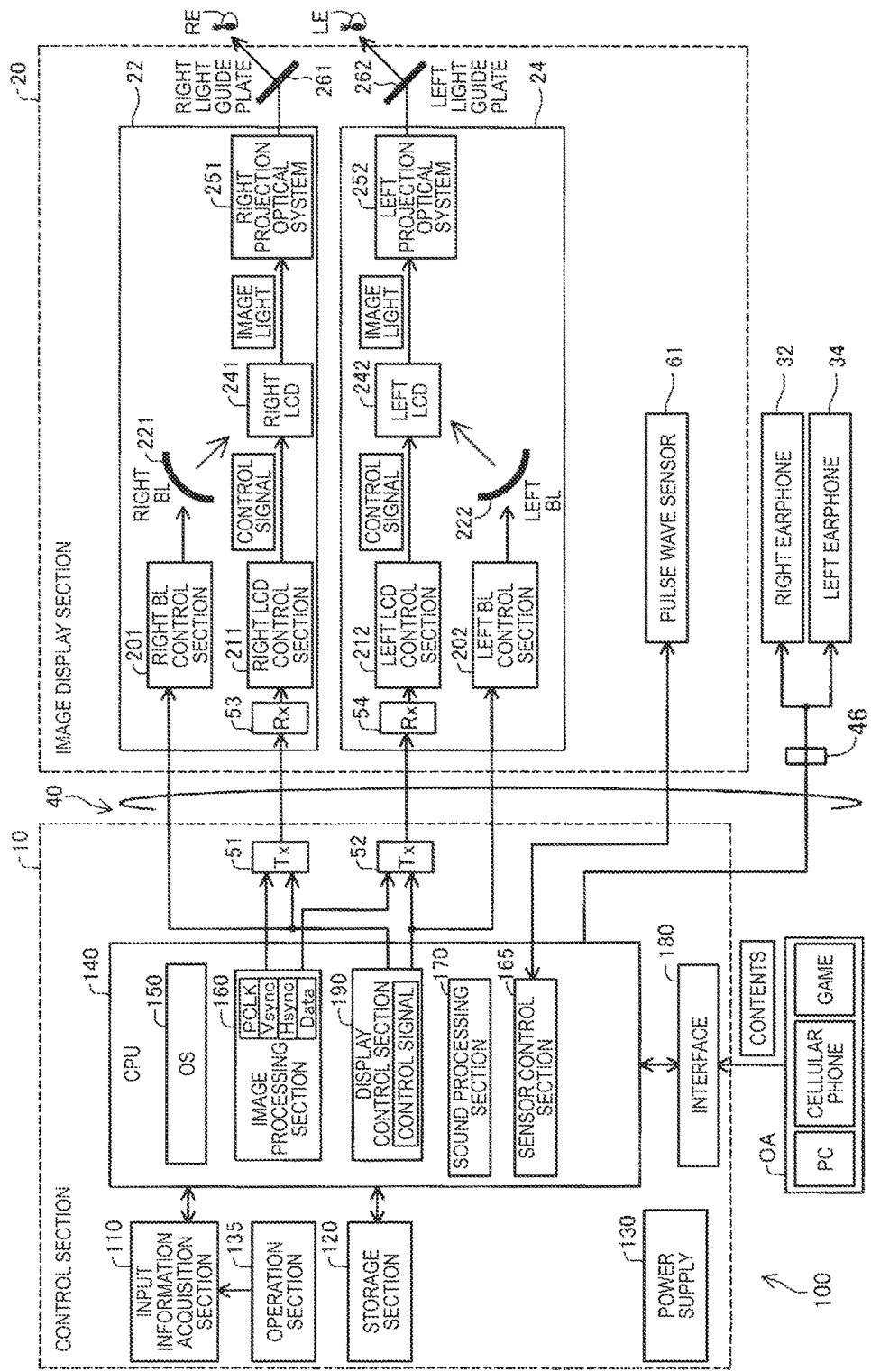
FIG. 2 is a block diagram functionally showing a configuration of the head-mount type display device.

FIG. 2 is a block diagram functionally showing a configuration of the head-mount type display device 100. As shown in FIG. 2, the control section 10 includes an input information acquisition section 110, a storage section 120, a power supply 130, an operation section 135, a CPU 140, an interface 180, a transmitting section 51 (Tx 51), and a transmitting section 52 (Tx 52). The operation section 135 receives the operation by the user, and includes the determination key 11, the display switching key 13, the track pad 14, the luminance switching key 15, the direction keys 16, the menu key 17, and the power switch 18.

The input information acquisition section 110 obtains the signal corresponding to the operation input by the user. As the signals corresponding to the operation inputs, there can be cited the signals corresponding to the operation inputs to, for example, the track pad 14, the direction keys 16, and the power switch 18 disposed in the operation section 135. The power supply 130 supplies each of the sections of the head-mount type display device 100 with the electrical power. As the power supply 130, a secondary cell, for example, can be used. The storage section 120 stores a variety of computer programs. The storage section 120 includes a ROM, a RAM, and so on. The CPU 140 retrieves and then executes the computer programs stored in the storage section 120 to thereby function as an operating system 150 (OS 150), a sensor control section 165, a display control section 190, a sound processing section 170, and an image processing section 160.

The sensor control section 165 analyzes the data (hereinafter also referred to simply as "pulse-wave waveform data") of the waveform of the pulse wave of the user detected by the pulse wave sensor 61. In the case in which a variation equal to or higher than a threshold value occurs in the waveform of the pulse wave based on the pulse-wave waveform data thus analyzed, the sensor control section 165 transmits the fact to each of the sections using a control signal. It should be noted that the pulse wave sensor 61 and the sensor control section 165 correspond to a detection section in the appended claims.

The display control section 190 generates control signals for controlling the right display drive section 22 and the left display drive section 24. Specifically, the display control section 190 controls to switch ON/OFF the drive of a right LCD 241 by a right LCD control section 211, to switch ON/OFF the drive of a right backlight 221 by a right backlight control section 201, to switch ON/OFF the drive of a left LCD 242 by a left LCD control section 212, to switch ON/OFF the drive of a left backlight 222 by a left backlight control section 202, and so on individually using the control signals. Thus, the display control section 190 controls generation and emission of the image light by each of the right display drive section 22 and the left display drive section 24. For example, the display control section 190 makes both of the right display drive section 22 and the left display drive section 24 generate image light, makes either of them generate the image light, or inhibits the both from generating the image light. Further, based on the control signal transmitted from the sensor control section 165, the display control section 190 generates control signals for making the image display section 20 display a predetermined message. It should be noted that the display control section 190 corresponds to a control section in the appended claims.

The display control section 190 transmits the control signals to the right LCD control section 211 and the left LCD control section 212 via the transmitting sections 51, 52, respectively. Further, the display control section 190 transmits the control signals to the right backlight control section 201 and the left backlight control section 202, respectively.

The image processing section 160 obtains the image signal included in the content. The image processing section 160 separates sync signals such as a vertical sync signal VSync and a horizontal sync signal HSync from the image signal thus obtained. Further, the image processing section 160 generates a clock signal PCLK using a phase locked loop (PLL) circuit or the like (not shown) in accordance with the periods of the vertical sync signal VSync and the horizontal sync signal HSync thus separated. The image processing section 160 converts the analog image signal, from which the sync signals are separated, into a digital image signal using an A/D conversion circuit or the like (not shown). Subsequently, the image processing section 160 stores the digital image signal obtained by the conversion into a DRAM in the storage section 120 frame by frame as the image data (RGB data) of the object image. It should be noted that it is also possible for the image processing section 160 to perform image processing such as a resolution conversion process, various color correction processes of, for example, adjustment of luminance and chromaticness, or a keystone distortion correction process on the image data if necessary.

The image processing section 160 transmits each of the clock signal PCLK, the vertical sync signal VSync, the horizontal sync signal HSync thus generated, and the image data, which is stored in the DRAM in the storage section 120, via each of the transmitting sections 51 and 52. It should be noted that the image data transmitted via the transmitting section 51 is also referred to as "right-eye image data," and the image data transmitted via the transmitting section 52 is also referred to as "left-eye image data." The transmitting sections 51, 52 function as transmitters for serial transmission between the control section 10 and the image display section 20.

The sound processing section 170 obtains a sound signal included in the content, amplifies the sound signal thus obtained, and then supplies it to a speaker (not shown) in the right earphone 32 and a speaker (not shown) in the left earphone 34 connected to the connecting member 46. It should be noted that in the case of, for example, adopting a Dolby (registered trademark) system, a process on the sound signal is performed, and sounds different from each other and with, for example, modified frequencies are output respectively from the right earphone 32 and the left earphone 34. Further, based on the control signal transmitted from the sensor control section 165, the sound processing section 170 makes the earphones 32, 34 output predetermined sounds.

The interface 180 is an interface for connecting various external equipment OA to be a supply source of contents to the control section 10. As the external equipment OA, there can be cited, for example, a personal computer (PC), a cellular phone terminal, and a game terminal. As the interface 180, there can be used, for example, a USB interface, a micro USB interface, and an interface for a memory card.

The image display section 20 is provided with the right display drive section 22, the left display drive section 24, a right light guide plate 261 as the right optical image display section 26, a left light guide plate 262 as the left optical image display section 28, and the pulse wave sensor 61.

The right display drive section 22 includes a receiving section 53 (Rx 53), the right backlight control section 201 (right BL control section 201) and the right backlight 221 (right BL 221) functioning as the light source, the right LCD control section 211 and the right LCD 241 functioning as the display element, and a right projection optical system 251. The right backlight control section 201 and the right backlight 221 function as the light source. The right LCD control section 211 and the right LCD 241 function as the display element. It should be noted that the right backlight control section 201, the right LCD control section 211, the right backlight 221, and the right LCD 241 are also collectively referred to as an "image light generation section."

The receiving section 53 functions as a receiver for serial transmission between the control section 10 and the image display section 20. The right backlight control section 201 drives the right backlight 221 based on the control signal input to the right backlight control section 201. The right backlight 221 is a light emitter such as an LED or electroluminescence (EL). The right LCD control section 211 drives the right LCD 241 based on the clock signal PCLK input via the receiving section 53, the vertical sync signal VSync, the horizontal sync signal HSync, and the right-eye image data. The right LCD 241 is a transmissive liquid crystal panel having a plurality of pixels arranged in a matrix.

The right projection optical system 251 is formed of a collimating lens for converting the image light emitted from the right LCD 241 into a light beam in a parallel state. The right light guide plate 261 as the right optical image display section 26 guides the image light, which is output from the right projection optical system 251, to the right eye RE of the user while reflecting the image light along a predetermined light path. It should be noted that the right projection optical system 251 and the right light guide plate 261 are also collectively referred to as a "light guide section."

The left display drive section 24 has substantially the same configuration as that of the right display drive section 22. The left display drive section 24 includes a receiving section 54 (Rx 54), the left backlight control section 202 (left BL control section 202) and the left backlight 222 (left BL 222) functioning as the light source, the left LCD control section 212 and the left LCD 242 functioning as the display element, and a left projection optical system 252. The left backlight control section 202 and the left backlight 222 function as the light source. The left LCD control section 212 and the left LCD 242 function as the display element. It should be noted that the left backlight control section 202, the left LCD control section 212, the left backlight 222, and the left LCD 242 are also collectively referred to as an "image light generation section." Further, the left projection optical system 252 is formed of a collimating lens for converting the image light emitted from the left LCD 242 into a light beam in a parallel state. The left light guide plate 262 as the left optical image display section 28 guides the image light, which is output from the left projection optical system 252, to the left eye LE of the user while reflecting the image light along a predetermined light path. It should be noted that the left projection optical system 252 and the left light guide plate 262 are also collectively referred to as a "light guide section."

Figure 3:
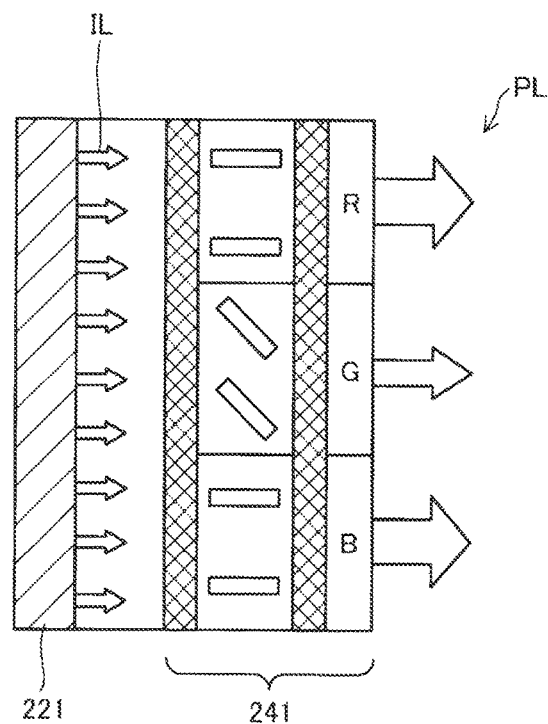
FIG. 3 is an explanatory diagram showing how image light is emitted by an image light generation section.

FIG. 3 is an explanatory diagram showing how the image light is emitted by the image light generation section. The right LCD 241 varies the transmission of the light transmitted through the right LCD 241 by driving the liquid crystal corresponding to each of the pixel positions arranged in a matrix to thereby modulate the illumination light IL, which is emitted from the right backlight 221, into valid image light PL representing the image. The same applies to the left side. It should be noted that although in the first embodiment, the backlight system is adopted as shown in FIG. 3, it is also possible to adopt a configuration of emitting the image light using a front light system or a reflective system.

A-2. Relationship Between Pulse Wave and Automatic Nervous System

Figure 4:
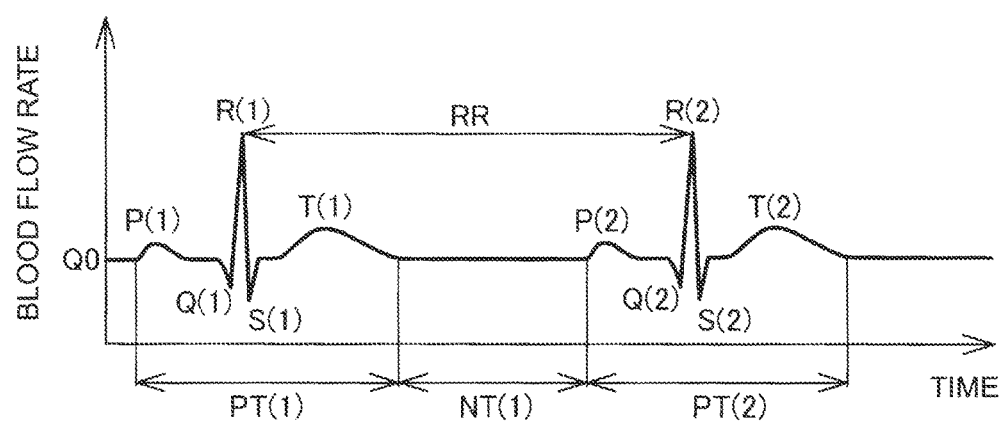
FIG. 4 is an explanatory diagram showing an example of pulse-wave waveform data.

It is known that when some failure occurs in the automatic nervous system of the user of the head-mount type display device 100, the fluctuation range of the heartbeat as one of biological information varies. FIG. 4 is an explanatory diagram showing an example of the pulse-wave waveform data. FIG. 4 shows the variation in the blood flow rate of the user thus obtained assuming that the horizontal axis represents the time axis. The waveform of the pulse wave is a waveform having a pulsation term PT and a non-pulsation term NT repeated alternately. In each of the pulsation terms PT, the blood flow rate varies with time in the order of an upward turning point P, a downward turning point Q, an upward turning point R, a downward turning point S, and an upward turning point T. It should be noted that the upward turning point P, the downward turning point Q, the upward turning point R, the downward turning point S, and the upward turning point T indicate the peaks where the difference in blood flow rate from the blood flow rate Q0 in the non-pulsation term NT becomes a maximum. The difference between the blood flow rate in the upward turning point R and the blood flow rate Q0 is greater than the difference between the blood flow rates in the upward turning point P, the downward turning point Q, the downward turning point S, and the upward turning point T and the blood flow rate Q0. Further, the interval between the upward turning point R(1) in a certain pulsation term PT(1) and the upward turning point R(2) in the subsequent pulsation term PT(2) corresponds to a pulse-wave R-R interval. In the case in which there is no circulatory system disease such as an irregular heartbeat, since it can be assumed that the pulsation and the heartbeat are equal to each other, it can be assumed that in the case in which the pulse-wave R-R interval is short, a heartbeat R-R interval is also short, and therefore, the number of beats of the heart per unit time is large, and in the case in which the pulse-wave R-R interval is long, the heartbeat R-R interval is also long, and therefore, the number of beats of the heart per unit time is small.

Figure 5:
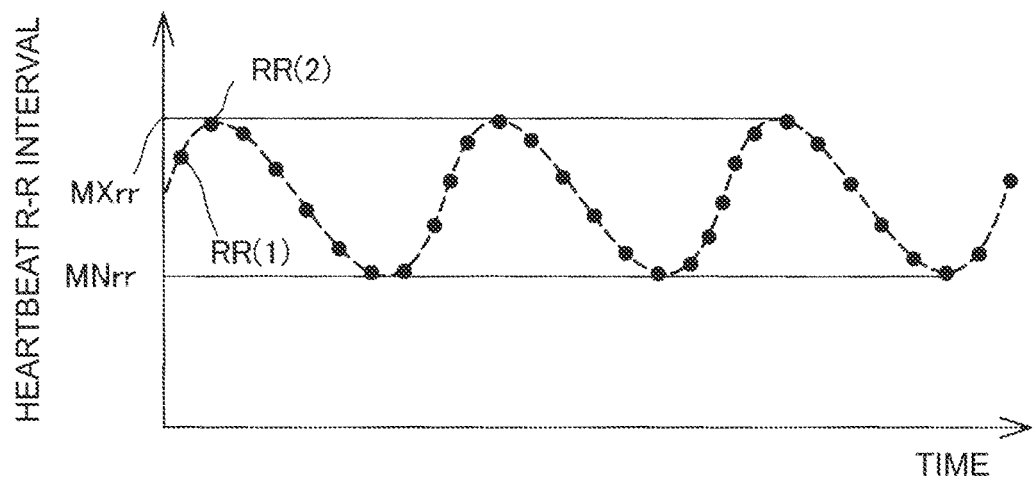
FIG. 5 is an explanatory diagram showing an example of a temporal transition of a heartbeat interval.

FIG. 5 is an explanatory diagram showing an example of a temporal transition of the heartbeat R-R interval. FIG. 5 shows a variation in the heartbeat R-R interval calculated from the pulse-wave waveform data of the user in good health condition assuming that the horizontal axis represents the time axis. It is known that the heartbeat R-R interval of the user in good health condition periodically varies in a range from about 900 milliseconds (ms) to about 950 ms. In the present specification, the difference between the maximum value MXrr and the minimum value MNrr of the heartbeat R-R interval in the predetermined number (e.g., 100 times) of beats of the heart is called a maximum difference DR in the heartbeat R-R interval. In the case of the user in good health condition, since the sympathetic nerve and the parasympathetic nerve are always acting to try to keep balance in the automatic nervous system, the heartbeat has a certain fluctuation, and the maximum difference DR in the heartbeat R-R interval is about 50 ms.

Figure 6:
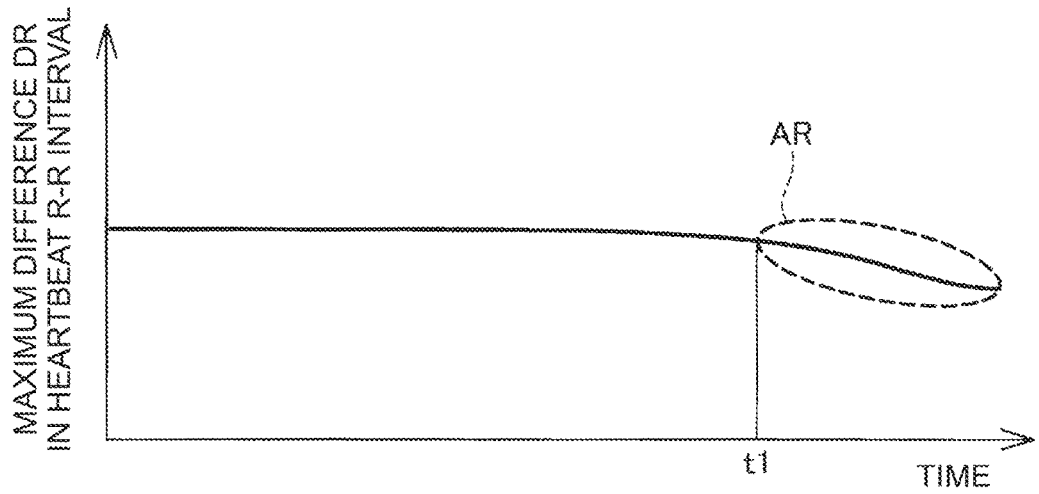
FIG. 6 is an explanatory diagram showing an example of a temporal transition of the maximum difference between the heartbeat intervals.

FIG. 6 is an explanatory diagram showing an example of a temporal transition of the maximum difference DR in the heartbeat R-R interval. It is known that in the case in which the health condition of the user fails to be kept in good condition, the automatic nervous system of the user fails to function normally, and the maximum difference DR in the heartbeat R-R interval decreases to approach zero, namely the heartbeat R-R interval approaches a constant value. As shown in FIG. 6, in a region AR after the time point t1, the maximum difference DR gradually decreases, which shows that some problem occurs in the automatic nervous system of the user in this case.

A-3. Display Control Process

Figure 7:
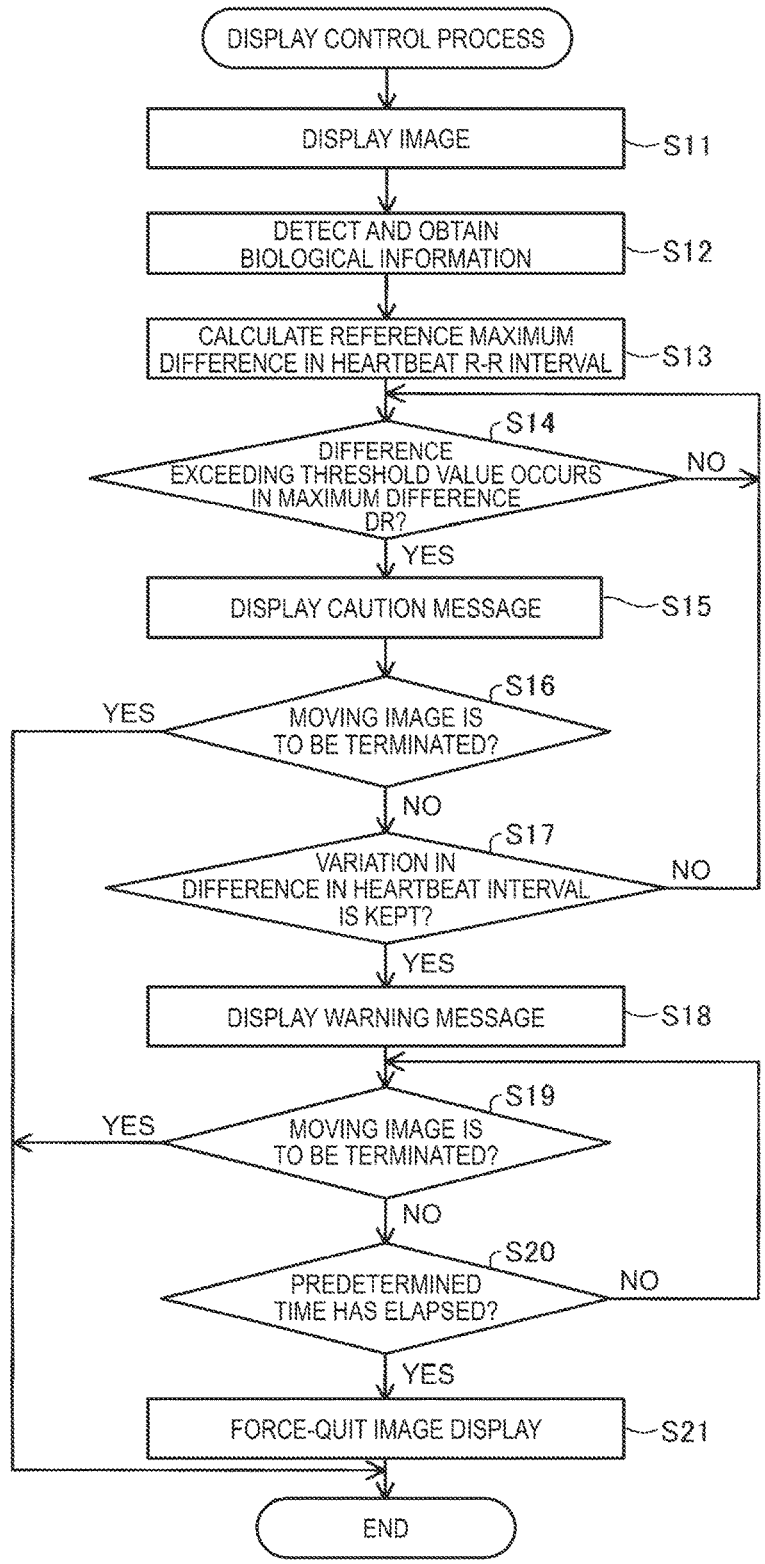
FIG. 7 is an explanatory diagram showing a flow of a display control process.

FIG. 7 is an explanatory diagram showing a flow of a display control process. The display control process is a process for displaying a predetermined message on the image display section 20 based on a variation in the waveform of the pulse wave, which is the biological information of the user and is detected after a moving image (an image) such as content starts being displayed on the image display section 20.

In the display control process, firstly, when the operation section 135 receives a predetermined operation for displaying an image on the image display section 20, the image is displayed (step S11) on the image display section 20 based on the operation thus received. When the image is displayed on the image display section 20, the pulse wave sensor 61 detects and then obtains (step S12) the pulse-wave waveform data as the biological information of the user. It should be noted that the pulse wave sensor 61 always obtains the pulse-wave waveform data in the case in which the image of the content is displayed on the image display section 20. Then, the sensor control section 165 calculates (step S13) the maximum difference DR in the heartbeat R-R interval to be the reference from the pulse-wave waveform data obtained until a predetermined time (e.g., 30 minutes) elapses from when the acquisition of the pulse-wave waveform data begins.

When the value of the maximum difference DR in the heartbeat R-R interval as the reference is calculated (step S13), the sensor control section 165 monitors (step S14) whether or not there occurs a difference equal to or greater than a threshold value (e.g., equal to or greater than 10% of the reference maximum, difference DR) between the reference maximum difference DR in the heartbeat R-R interval and the maximum difference DR in the heartbeat R-R interval obtained in the predetermined period (e.g., one minute). In the case in which the difference equal to or greater than the threshold value is not detected in the difference in the maximum difference DR in the heartbeat R-R interval (NO in the step S14), the sensor control section 165 continues to monitor (step S14) occurrence of the difference equal to or greater than the threshold value in the maximum, difference DR in the heartbeat R-R interval. In the case in which the difference equal to or greater than the threshold value has been detected in the maximum difference DR in the heartbeat R-R interval (YES in the step S14), the display control section 190 makes the image display section 20 display (step S15) a caution message stating that the moving image of the content is to be terminated.

Figure 8:
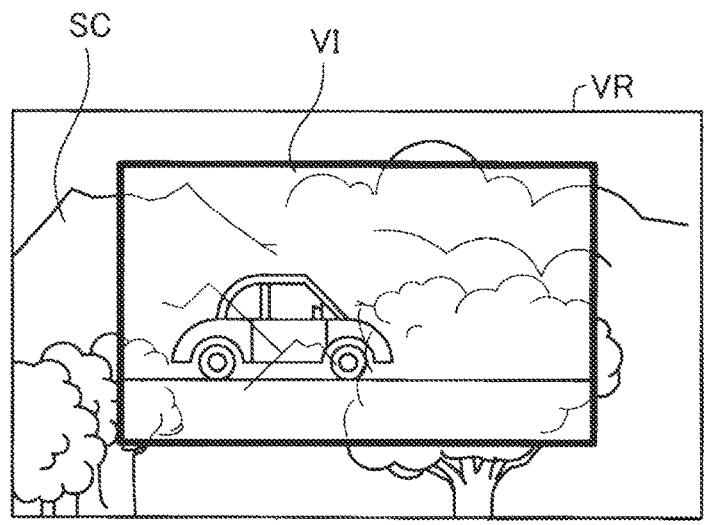
FIG. 8 is an explanatory diagram showing an example of a visual field to be visually recognized by the user.
Figure 9:
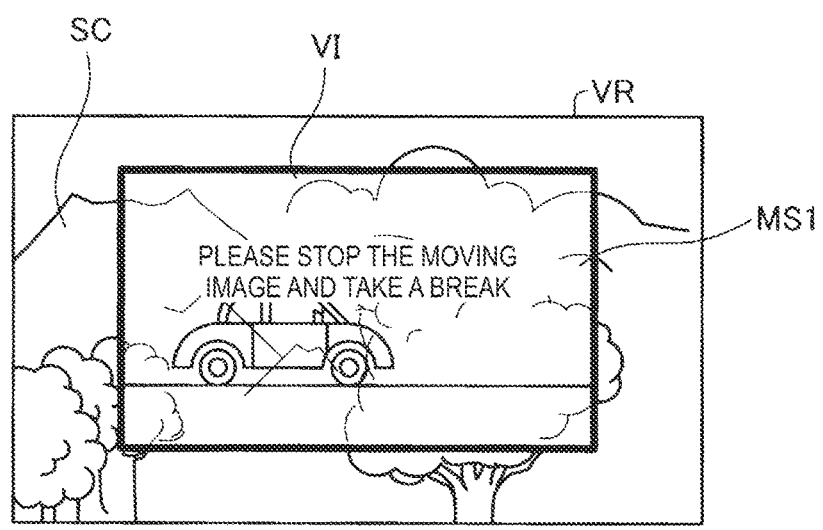
FIG. 9 is an explanatory diagram showing an example of a visual field to be visually recognized by the user.

FIGS. 8 and 9 are explanatory diagrams each showing an example of a visual field VR to be visually recognized by the user. FIG. 8 shows the visual field VR before the caution message is displayed on the image display section 20, and FIG. 9 shows the visual field VR after the caution message is displayed on the image display section 20. As shown in FIG. 8, the visual field VR to be visually recognized by the user includes an external sight SC and the display image VI. The user can also visually recognize the external sight SC in a superimposed manner in the range of the display image VI. The visual field VR shown in FIG. 9 is different from the visual field VR shown in FIG. 8 only in the point that the caution message MS1 is included, and is the same in the other points. As shown in FIG. 9, the display control section 190 makes the image display section 20 display a sentence "PLEASE STOP THE MOVING IMAGE AND TAKE A BREAK" as the caution message MS1. It should be noted that the display control section 190 and the image display section 20 correspond to an annunciation section in the appended claims.

After the caution message MS1 is displayed on the image display section 20 (step S15 in FIG. 7), the operation section 135 monitors (step S16) an operation for termination of the moving image displayed on the image display section 20. When the operation for the termination of the moving image is performed (YES in the step S16), the control section 10 terminates the display control process.

If the operation for the termination of the moving image is not performed in the process of the step S16 (NO in the step S16), the sensor control section 165 determines (step S17) whether or not the maximum difference DR in the heartbeat R-R interval is kept in the state in which the difference equal to or greater than the threshold value continues to occur. In the case in which the difference equal to or greater than the threshold value does not occur in the maximum difference DR in the heartbeat R-R interval (NO in the step S17), the sensor control section 165 further monitors (step S14) occurrence of the difference equal to or greater than the threshold value in the maximum difference DR in the heartbeat R-R interval.

Figure 10:
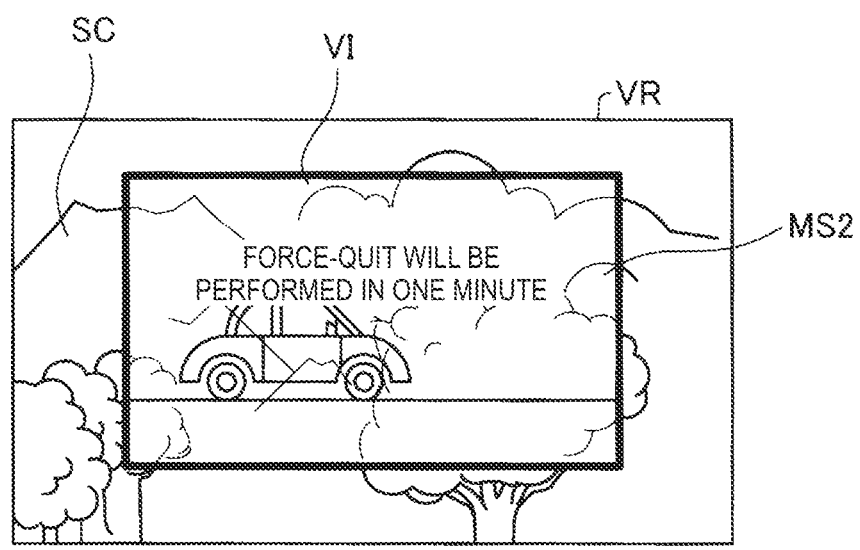
FIG. 10 is an explanatory diagram showing an example of a visual field to be visually recognized by the user.

In the case in which the difference equal to or greater than the threshold value has been detected in the maximum difference DR in the heartbeat R-R interval in the process of the step S17 (YES in the step S17), the display control section 190 makes the image display section 20 display (step S18) a warning message stating that the moving image of the content will be force-quit. FIG. 10 is an explanatory diagram showing an example of a visual field VR to be visually recognized by the user. As shown in FIG. 10, the visual field VR of the user includes the warning message MS2 of "FORCE-QUIT WILL BE PERFORMED IN ONE MINUTE" to be displayed by the image display section 20.

After the warning message MS2 is displayed on the image display section 20 (step S18 in FIG. 7), the operation section 135 monitors (step S19) an operation for termination of the moving image displayed on the image display section 20. When the operation for the termination of the moving image is performed (YES in the step S19), the control section 10 terminates the display control process.

In the case in which the operation for the termination of the moving image is not performed in the process of the step S19 (NO in the step S19), the display control section 190 waits (step S20) until one minute, namely a predetermined time, elapses from when the image display section 20 has been made to display the warning message MS2. In the case in which the predetermined time has not yet elapsed (NO in the step S20), the display control section 190 continues to monitor (step S19) the operation for the termination of the moving image. If the predetermined time has elapsed (YES in the step S20), the display control section 190 performs (step S21) the force-quit for hiding the moving image of the content having been displayed on the image display section 20, and then the control section 10 terminates the display control process. It should be noted that the caution message MS1 and the warning message MS2 correspond to image control information in the appended claims.

As explained hereinabove, in the head-mount type display device 100 according to the first embodiment, the pulse wave sensor 61 detects and then obtains the pulse-wave waveform data as the biological information of the user, and then the sensor control section 165 calculates the maximum difference DR in the heartbeat R-R interval. In the case in which the difference equal to or greater than the threshold value is detected in the maximum difference DR in the heartbeat R-R interval, the image display section 20 displays the caution message MS1 or the warning message MS2. Therefore, in the head-mount type display device 100 according to the first embodiment, since the control of the display image is performed in accordance with the individual difference between the users based on the malfunction of the automatic nervous system detected in the individual user, convenience of the user can be enhanced.

Further, in the head-mount type display device 100 according to the first embodiment, since the caution message MS1 and the warning message MS2 are displayed on the image display section 20 based on the maximum difference DR in the heartbeat R-R interval in the pulse-wave waveform data detected, the variation in the automatic nervous system of the user can easily be detected, and thus, the convenience of the user can further be enhanced. Further, since no large-size equipment is required for detecting the variation in the automatic nervous system of the user, the convenience of the user can be enhanced while inhibiting the portability of the image display section 20 from degrading.

Further, in the head-mount type display device 100 according to the first embodiment, the caution message MS1 and the warning message MS2 are displayed on the image display section 20 to thereby prompt the user to stop viewing the content using the visual information. Therefore, in the head-mount type display device 100 according to the first embodiment, it is easy for the user to visually recognize the caution message MS1 and the warning message MS2, and thus, the convenience of the user can further be enhanced.

Further, in the head-mount type display device 100 according to the first embodiment, the force-quit of the moving image is performed in the case in which the operation for the termination of the moving image displayed on the image display section 20 after the warning message MS2 is displayed on the image display section 20. Therefore, in the head-mount type display device 100 according to the first embodiment, since the display image is terminated to achieve restoration of the health condition of the user in the case in which the malfunction of the automatic nervous system of the user, physical deconditioning of the user, or the like is detected, the convenience of the user can further be enhanced.

B. Second Embodiment

Figure 11:
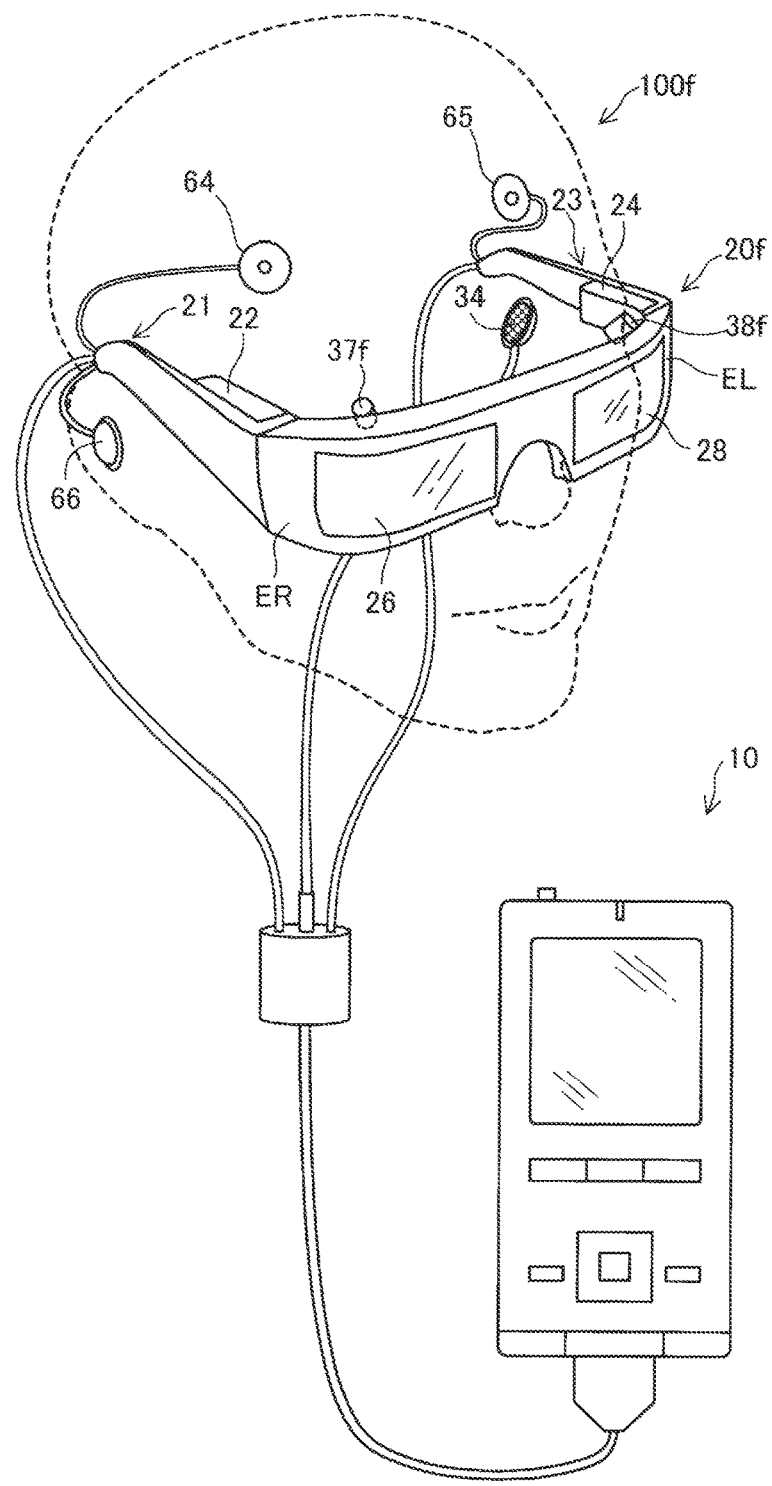
FIG. 11 is an explanatory diagram showing an exterior configuration of a head-mount type display device according to a second embodiment of the invention.
Figure 12:
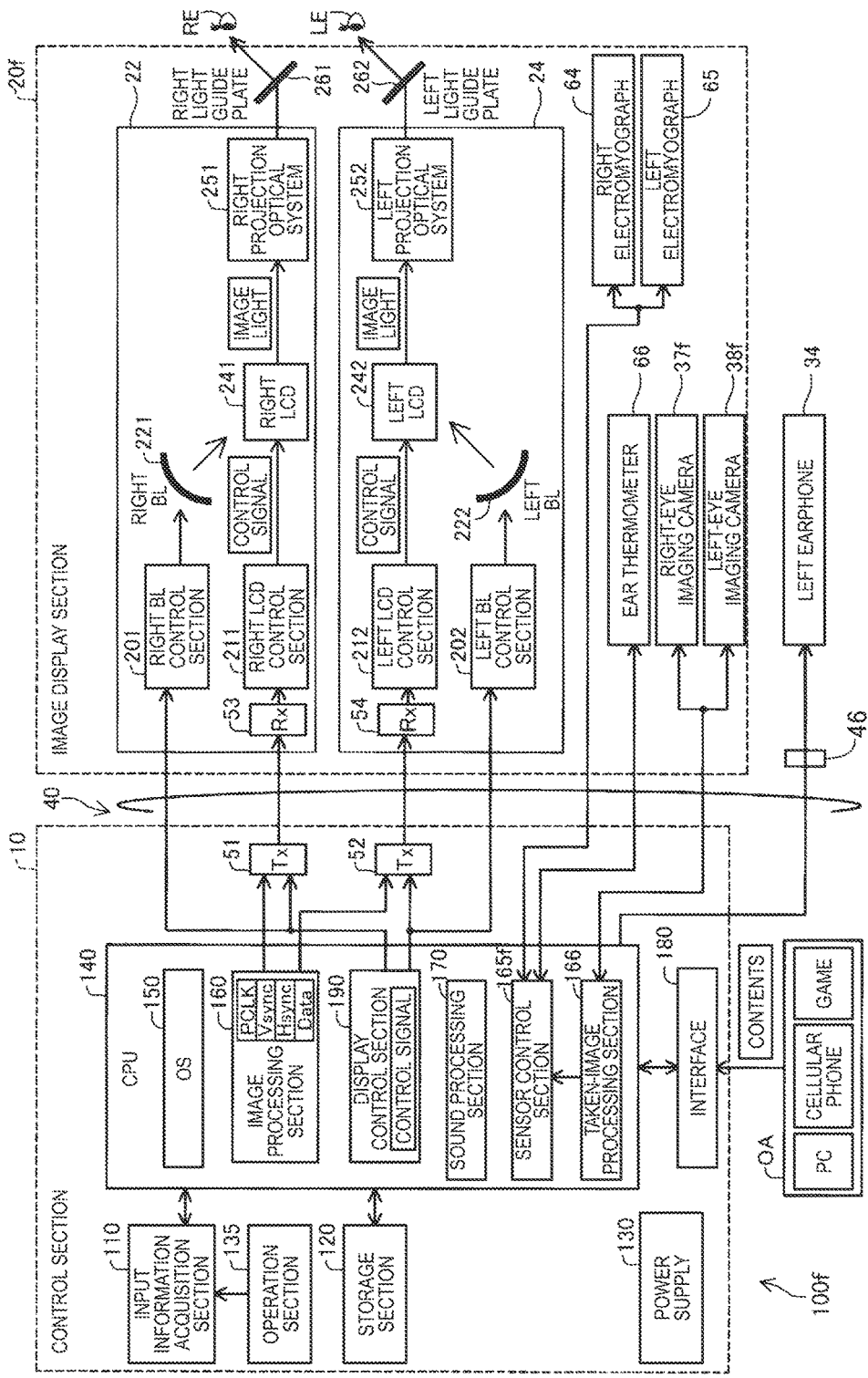
FIG. 12 is a block diagram functionally showing a configuration of the head-mount type display device according to the second embodiment.

FIG. 11 is an explanatory diagram showing an exterior configuration of a head-mount type display device 100*f* according to a second embodiment. FIG. 12 is a block diagram functionally showing a configuration of the head-mount type display device 100*f* according to the second embodiment. As shown in FIGS. 11 and 12, in the head-mount type display device 100*f* according to the second embodiment, there are disposed an ear thermometer 66, a right electromyograph 64, a left electromyograph 65, a right-eye imaging camera 37*f*, and a left-eye imaging camera 38*f* instead of the pulse wave sensor 61 of the first embodiment. Further, as shown in FIG. 12, a control section 10*f* of the second embodiment includes a taken-image processing section 166 for processing the images taken by the right-eye imaging camera 37*f* and the left-eye imaging camera 38*f*.

The ear thermometer 66 is a thermometer to be inserted into an earhole of the user to thereby measure the body temperature of the user. It should be noted that the measurement of the body temperature denotes the measurement of the body temperature in the Celsius' temperature scale, and can also be rephrased as identification of the degree of the body temperature. In the second embodiment, the ear thermometer 66 is disposed as a substitute for the right earphone 32 of the first embodiment. It should be noted that unlike the first embodiment, the left earphone 34 is a monaural earphone for outputting sounds in the second embodiment.

The right electromyograph 64 is an electromyograph using a surface electrode to be mounted in the vicinity of the right temple of the user. The right electromyograph 64 makes an electric current flow in the vicinity of the temple where the right electromyograph 64 is mounted, and then detects a value of the voltage thus generated to thereby identify the expansion and contraction of the external ocular muscle and the internal ocular muscle for moving the right eye RE of the user. When the external ocular muscle and the internal ocular muscle expand or contract, the voltage value to be detected varies. The right electromyograph 64 transmits the voltage value thus detected to the sensor control section 165*f* as the control signal. The left electromyograph 65 is an electromyograph using a surface electrode to be mounted in the vicinity of the left temple of the user. Similarly to the right electromyograph 64, the left electromyograph 65 identifies the expansion and contraction of the external ocular muscle and the internal ocular muscle of the left eye LE of the user. Further, the left electromyograph 65 transmits the voltage value thus detected to the sensor control section 165*f* as the control signal. Hereinafter, the right electromyograph 64 and the left electromyograph 65 are also simply referred to collectively as electromyographs 64, 65. As shown in FIG. 11, the electromyographs 64, 65 are each formed so as to be able to keep the state of having contact with the user.

The right-eye imaging camera 37*f* is a camera for imaging the right eye RE of the user. Further, the left-eye imaging camera 38*f* is a camera for imaging the left eye LE of the user. The right-eye imaging camera 37*f* and the left-eye imaging camera 38*f* transmit the image signal representing the images thus taken with R, G, and B components to the taken-image processing section 166. It should be noted that hereinafter the right-eye imaging camera 37*f* and the left-eye imaging camera 38*f* are also simply referred to collectively as eye imaging cameras 37*f*, 38*f*.

The taken-image processing section 166 performs binarization for identifying pixels to be identified as a red color on the images based on the image signal transmitted from the eye imaging cameras 37*f*, 38*f*. The taken-image processing section 166 performs the binarization of identifying the pixels with, for example, the red component (the R component) of not lower than 150, the green component (the G component) of not higher than 100, and the blue component (the B component) of not higher than 100 as the red pixels, and identifying the other pixels as the pixels with the colors other than red. The taken-image processing section 166 transmits the result of the binarization performed on the taken images to the sensor control section 165*f*.

Further, the sensor control section 165*f* performs the Fourier transformation (FT) on the voltage values transmitted from the electromyographs 64, 65 to decompose the variation in the voltage value with time into intensities in the respective frequencies. In the case in which the fatigue is accumulated in the user, for example, since the external ocular muscle twitches, the sensor control section 165*f* detects the high-frequency variation in the voltage value in some cases.

Further, in the case where the variation of increasing the proportion of the pixels having been identified as the red pixels is detected in the result of the binarization on the pixels of the taken images transmitted from the taken-image processing section 166, the sensor control section 165*f* determines that the area of the red blood vessels in the eyes of the user increases. In other words, since in this case, it is conceivable that the degree of the redness of the eyes of the user becomes worse, the sensor control section 165*f* determines that an abnormality occurs in the user. It should be noted that the identification of the redness of the eyes in the appended claims includes identification of the degree of the redness of the eyes in addition to the determination on whether or not the eyes are red.

Figure 13:
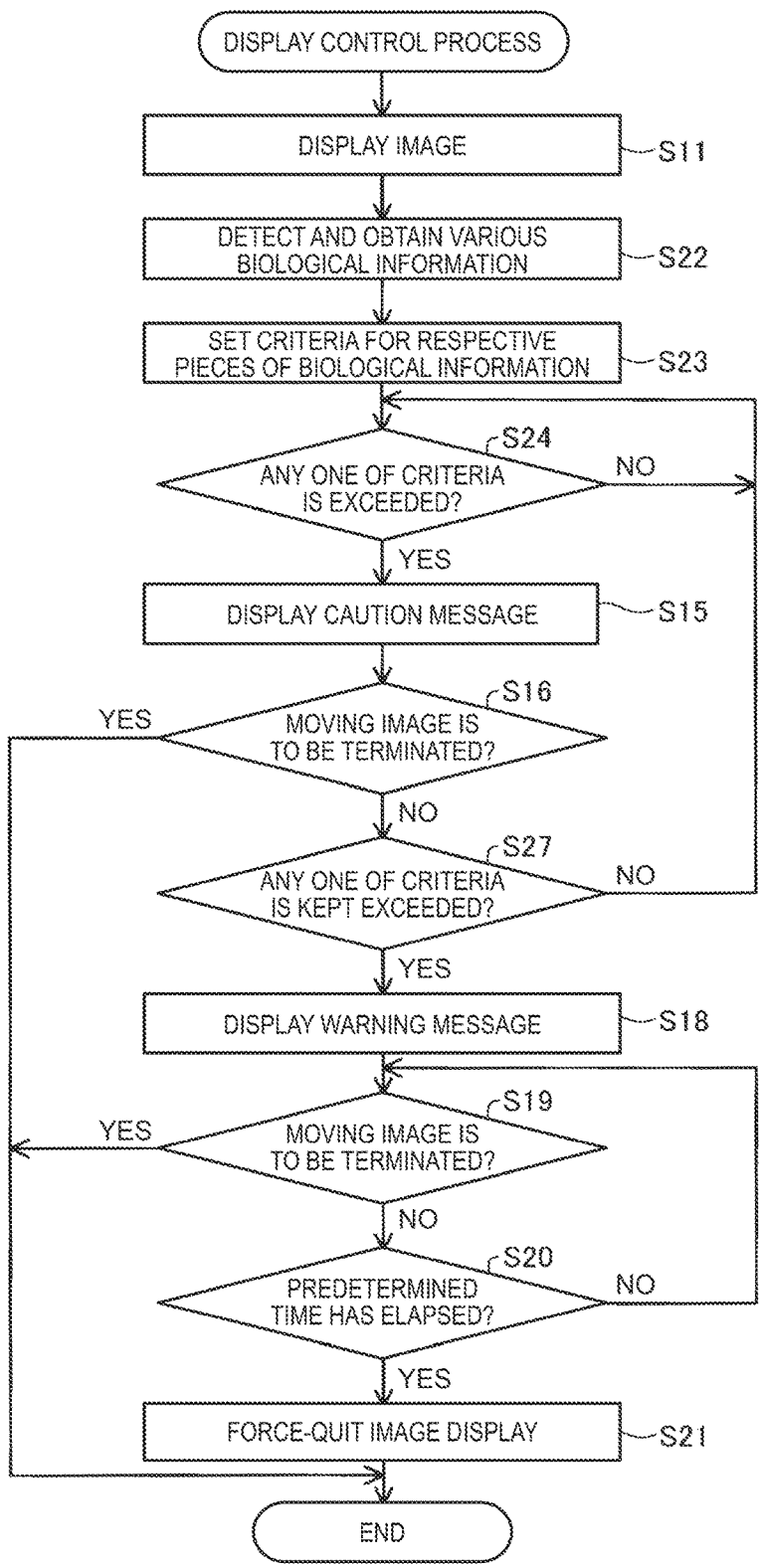
FIG. 13 is an explanatory diagram showing a flow of a display control process according to the second embodiment.

FIG. 13 is an explanatory diagram showing a flow of a display control process according to the second embodiment. The display control process according to the second embodiment is different in the steps S12, S13, S14, and S17 from the first embodiment shown in FIG. 7, and is the same in the other steps as the first embodiment. In the display control process, when the image is displayed (step S11) on the image display section 20, the sensor control section 165*f* detects and then obtains (step S22) the body temperature using the ear thermometer 66, the intensities in the respective frequencies based on the expansion and contraction of the external ocular muscle and the internal ocular muscle using the electromyographs 64, 65, and the proportion of the red pixels in the taken images using the eye imaging cameras 37*f*, 38*f* and the taken-image processing section 166 as the biological information of the user.

Subsequently, the sensor control section 165*f* sets (step S23) criteria for the respective pieces of the biological information thus obtained. The sensor control section 165*f* periodically (e.g., every 30 seconds) obtains and then stores the body temperature of the user measured by the ear thermometer 66. The sensor control section 165*f* starts obtaining the body temperature after the head-mount type display device 100*f* is started up, and then calculates the average body temperature as an average value in five minutes. The sensor control section 165*f* sets the body temperature (hereinafter also referred to as an "abnormal body temperature") 2 degrees in the Celsius' temperature scale (2° C.) or higher or lower than the average body temperature as a threshold value of the criterion of the body temperature. Further, the sensor control section 165*f* sets a threshold value of the criterion to 110% of the average proportion of the number of the red pixels to the total number of pixels in the taken images taken for 5 minutes after the periodic (every 30 seconds) imaging of the images of the both eyes of the user is started. Further, the sensor control section 165*f* sets a frequency, which is a predetermined value or higher than the value obtained by performing the Fourier transformation on the voltage values obtained by the electromyographs 64, 65, and an intensity, which is a predetermined value or higher than that value, as threshold values of the criteria.

Then, the sensor control section 165*f* determines (step S24) whether or not the value detected by any one of the sensors among the three pieces of the biological information exceeds the criterion thus set. For example, in the case in which the body temperature equal to or 2 degrees higher than the average body temperature is detected (YES in the step S24), the sensor control section 165*f* determines that an abnormality occurs in the physical condition of the user, and then displays (step S15) the caution message.

Further, in a similar manner, the sensor control section 165*f* displays the caution message also in the case in which the value exceeding the criterion thus set is detected in another piece of the biological information. For example, in the case in which a threshold anomaly occurs in the proportion of the number of the red pixels in the taken images of the eye imaging cameras 37*f,* 38*f* (YES in the step S24), the sensor control section 165*f* determines that the degree of the redness of the eyes of the user is getting worse, and then displays (step S15) the caution message. Further, in the case in which the sensor control section 165*f* detects a frequency, which is a predetermined value or higher than the value obtained by performing the Fourier transformation on the voltage values obtained by the electromyographs 64, 65, and an intensity, which is a predetermined value or higher than that value (YES in the step S24), the sensor control section 165*f* determines that an abnormality occurs in the external ocular muscle or the internal ocular muscle of the user, and then displays (step S15) the caution message.

In the case in which the operation of terminating the moving image is not performed in the process of the step S16 (NO in the step S16), the sensor control section 165*f* determines (step S27) whether or not the biological information having exceeded the criterion thus set keeps exceeding the criterion, and a variety of processes are then performed.

As explained hereinabove, in the head-mount type display device 100*f* according to the second embodiment, the sensor control section 165*f* determines the degree of the redness of the eyes of the user based on the rate of the pixels as the biological information obtained by the taken-image processing section 166 binarizing the taken images of the both eyes, and then performs the display control process. Therefore, in the head-mount type display device 100*f* according to the second embodiment, since the degree of the devotion of the user to the display image and the viewing time are estimated by determining the degree of the redness of the eyes of the user, and the control of the display image is performed based on the variation in physical condition detected in the individual user, the convenience of the user can be enhanced.

Further, in the head-mount type display device 100*f* according to the second embodiment, the sensor control section 165*f* detects an abnormality in the physical condition of the user based on the variation in electromyogram as the biological information of the user based on the motion of the external ocular muscle or the internal ocular muscle for moving the eyes of the user, and then performs the display control process. Therefore, since in the head-mount type display device 100*f* according to the second embodiment, the fatigue accumulated in the external ocular muscle or the internal ocular muscle of the user is determined, and the control of the display image is performed in accordance with the fatigue of the eyes corresponding to the individual difference between the users, the convenience of the user can be enhanced.

Further, in the head-mount type display device 100*f* according to the second embodiment, the electromyographs 64, 65 are each formed so as to be able to keep the state of having contact with the user. Therefore, in the head-mount type display device 100*f* according to the second embodiment, the biological information of the user can more easily be detected in more detail, and the control corresponding to the biological information of the user is easy to perform.

Further, in the head-mount type display device 100*f* according to the second embodiment, the sensor control section 165*f* detects an abnormal body temperature of the user based on the body temperature of the user as the biological information of the user measured by the ear thermometer 66, and then performs the display control process. Therefore, since in the head-mount type display device 100*f* according to the second embodiment, the control of the display image is performed in accordance with the variation in the body temperature of the individual user, the convenience of the user can be enhanced.

C. Modified Examples

It should be noted that the invention is not limited to the embodiments described above, but can be implemented in various forms within the scope or the spirit of the invention, and the following modifications, for example, are also possible.

C1. Modified Example 1

Figure 14:
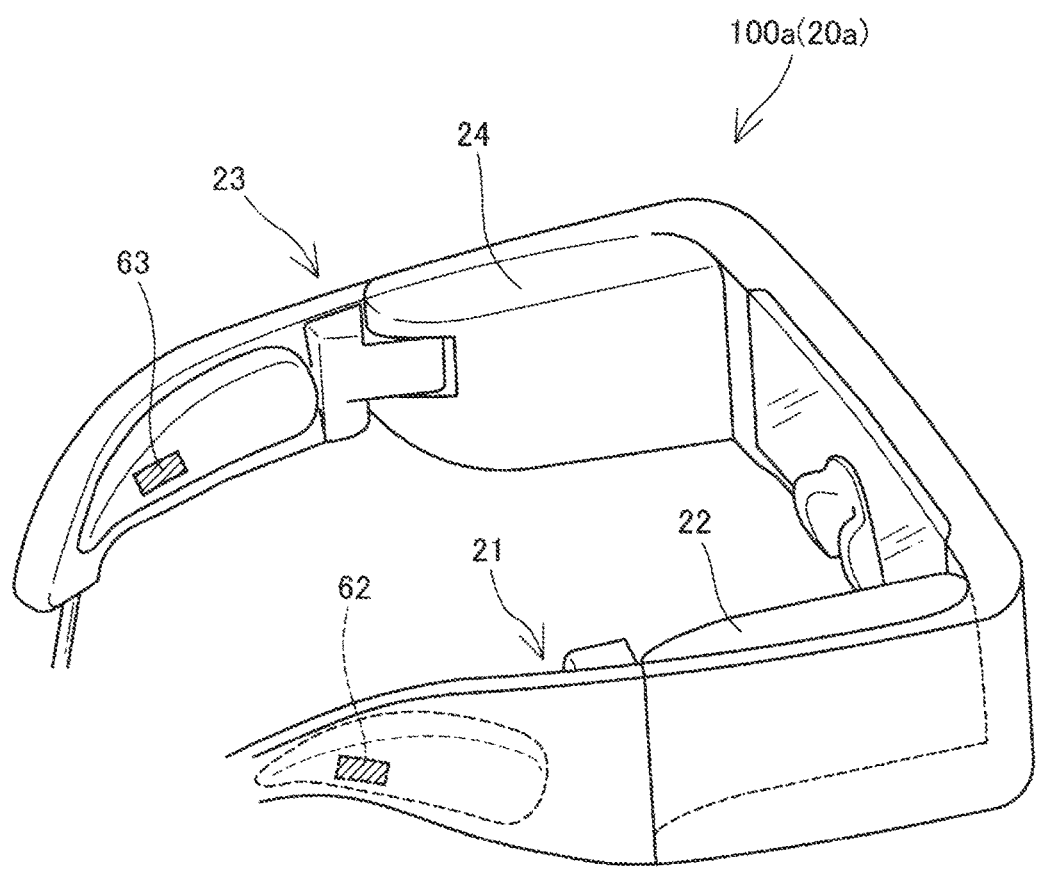
FIG. 14 is an explanatory diagram showing an exterior configuration of a head-mount type display device according to a modified example.
Figure 15:
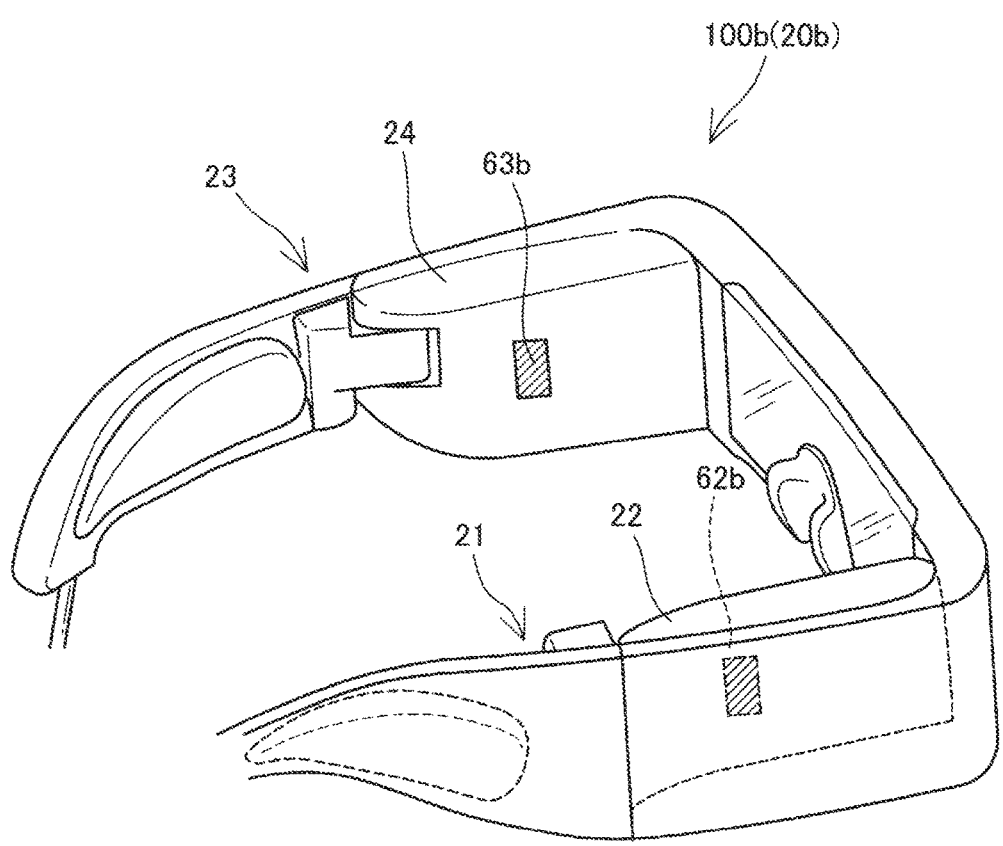
FIG. 15 is an explanatory diagram showing an exterior configuration of a head-mount type display device according to a modified example.

FIGS. 14 and 15 are explanatory diagrams each showing an exterior configuration of a head-mount type display device according to a modified example. The head-mount type display device 100*a* and the head-mount type display device 100*b* according to the present modified example are each different in the position at which the pulse wave sensor 61 is disposed in the image display section 20 from the head-mount type display device 100 according to the embodiment described above, and are the same in the other points as in the embodiment described above. As shown in FIG. 14, in the head-mount type display device 100*a*, the pulse wave sensor 62 is disposed at the position, which faces a portion located above the right ear of the user when the user wears the image display section 20 on the head, and the pulse wave sensor 63 is disposed at the position, which faces a portion located above the left ear of the user. Further, as shown in FIG. 15, in the head-mount type display device 100*b*, the pulse wave sensor 62*b* is disposed at the position, which faces the right temple of the user when the user wears the image display section 20 on the head, and the pulse wave sensor 63*b* is disposed at the position, which faces the left temple of the user. Although in this modified example, the pulse wave sensors 62, 63, 62*b*, and 63*b* are disposed at the positions different from that of the pulse wave sensor 61 in the embodiment described above, these head-mount type display devices 100*a*, 100*b* can also detect the pulse wave of the user. It should be noted that although in the head-mount type display devices 100*a*, 100*b*, the pulse wave sensors are disposed on the right and the left in the image display section 20, it is also possible to dispose the pulse wave sensor at either one of the positions, or at another position.

C2. Modified Example 2

Figure 16:
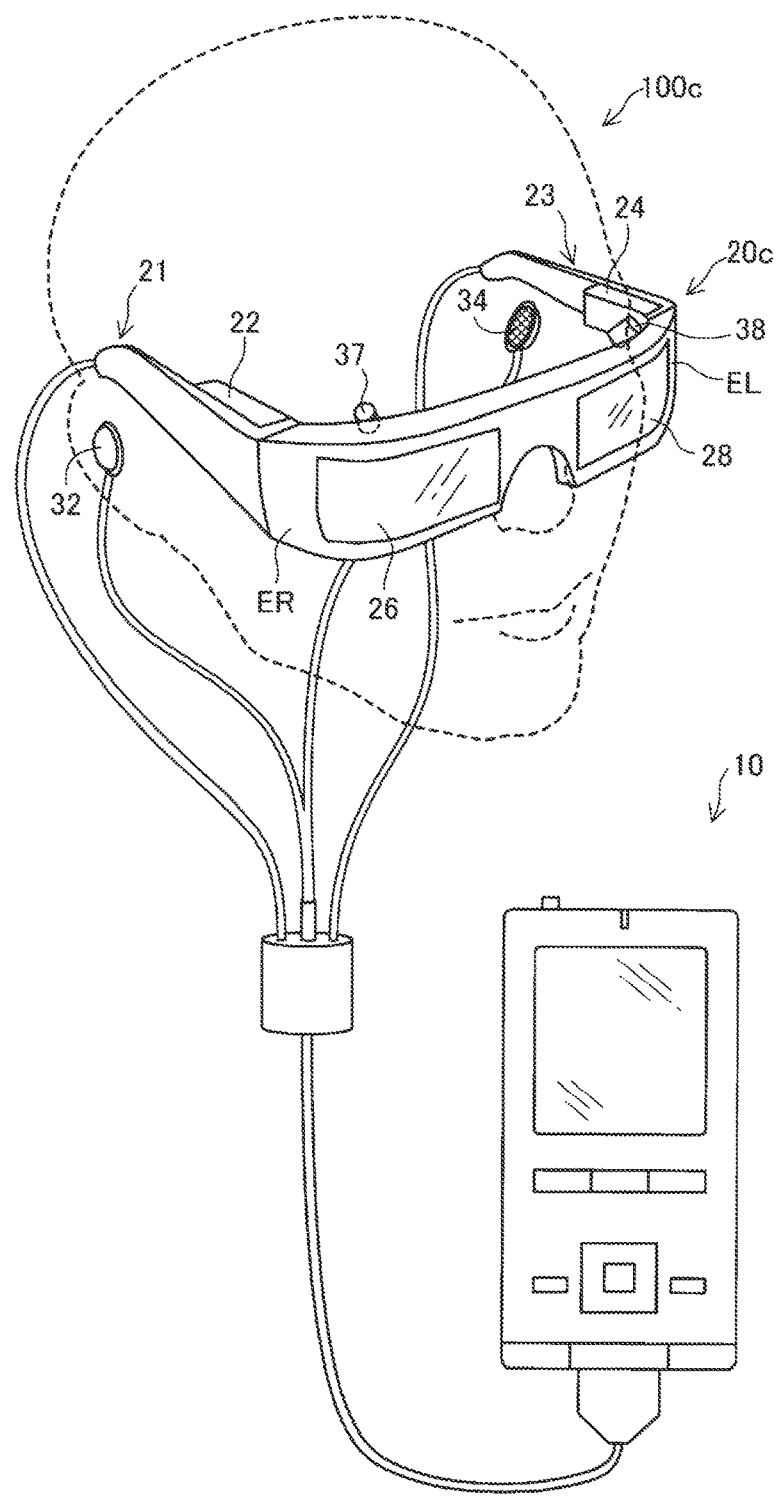
FIG. 16 is an explanatory diagram showing an exterior configuration of a head-mount type display device according to a modified example.

FIG. 16 is an explanatory diagram showing an exterior configuration of a head-mount type display device 100*c* according to a modified example. As shown in FIG. 16, the head-mount type display device 100*c* is different in the point that a right-eye imaging camera 37 and a left-eye imaging camera 38 are disposed in the image display section 20 instead of the pulse wave sensor 61 from the device of the embodiment described above, and is the same in the other parts of the configuration as in the embodiment described above. It should be noted that the right-eye imaging camera 37 and the left-eye imaging camera 38 are also simply referred to collectively as "eye imaging cameras." The right-eye imaging camera 37 and the left-eye imaging camera 38 are small-sized CCD cameras for respectively imaging the right eye and the left eye of the user. In the head-mount type display device 100*c*, the sensor control section 165 analyzes the images of the right eye and the left eye of the user respectively taken by the eye imaging cameras 37, 38 to thereby determine an open-close condition of the eyelid of each of the right eye and the left eye. The sensor control section 165 performs pattern matching of the open-close state of the eyelid on each of the right eye and the left eye of the user taken by the eye imaging cameras 37, 38 to determine the state in which the eyelid is closed, the half-closed state in which the eyelid is half-closed, and so on. Further, the sensor control section 165 measures the size of the pupil in each of the right eye and the left eye of the user by performing pattern matching.

If the user devotes him or herself too much to the moving image of the content presently displayed on the image display section 20, the number of times of the blink per unit time decreases, and there is a possibility of causing a state such as dry eye. Therefore, in the head-mount type display device 100*c*, it is also possible for the sensor control section 165 to calculate (step S13) the number of times of the blink per unit time obtained in the predetermined period in the process of the steps S13 and S14 in FIG. 7, and monitor (step S14) whether or not the number of times of the blink per unit time has decreased by a value exceeding a predetermined threshold.

Further, it is known that if the sympathetic nerve as one of the automatic nervous systems fires, the pupil opens more widely compared to the state in which the sympathetic nerve does not fire. Therefore, in the head-mount type display device 100*c*, it is also possible for the sensor control section 165 to calculate (step S13) the size of the pupil obtained in a predetermined period, and to monitor (step S14) whether or not the size of the pupil varies by a value equal to or larger than a predetermined threshold value. In the head-mount type display device 100*c* according to this modified example, unlike the embodiment described above, it is possible to control the image to be displayed on the image display section 20 based on the images obtained by the eye imaging cameras 37, 38 even if the pulse-wave data is not obtained. It should be noted that although in the head-mount type display device 100*c*, the eye imaging cameras 37, 38 are used as the detection section for detecting the biological information, the open-close state of the eyes of the user can be detected by an infrared sensor. In the head-mount type display device 100*c* according to this modified example, the caution message MS1 and the warning message MS2 are displayed on the image display section 20 based on the open-close state of the eyes of the user or the state of the pupils. Therefore, since the control of the display image is performed in accordance with the individual difference between the users based on the malfunction of the automatic nervous system detected in the individual user, the convenience of the user can be enhanced.

C3. Modified Example 3

Although in the embodiment described above, the caution message MS1 and the warning message MS2 stating the termination of the moving image of the content displayed on the image display section 20 are displayed as the images, the method of prompting the stoppage of viewing of the content presently viewed by the user is not limited to the above, but can variously be modified. For example, it is also possible for the sound processing section 170 to output sounds related to the stoppage of viewing of the content to the user using the earphones 32, 34 instead of the caution message MS1 and the warning message MS2. In this modified example, since it is possible to call attention to the user while preventing the display image presently viewed by the user from being interfered, the convenience of the user can be enhanced.

Further, although in the embodiment described above, the image display section 20 is made to display the caution message MS1 and the warning message MS2 as the information related to the control of the image to be displayed on the image display section 20, the invention is not limited to this configuration, but can variously be modified. For example, a message for decreasing the luminance of at least one of the right backlight 221 and the left backlight 222 can also be displayed on the image display section 20. In the present modified example, the load of the user can be reduced by decreasing the luminance of the image light to thereby restore the automatic nervous system to the normal state without halting the reproduction of the moving image of the content.

C4. Modified Example 4

Although in the embodiment described above, the difference between the maximum value MXrr and the minimum value MNrr of the heartbeat R-R interval in the 100 pulses of the heart is cited as an example of the maximum difference DR in the heartbeat R-R interval, the maximum difference DR is not limited to this example, but can variously be modified. For example, 50 pulses or 200 pulses of the heart can also be adopted, or a difference between the maximum value MXrr and the minimum value MNrr of the heartbeat R-R interval in the pulses of the heart included in the unit time can also be adopted. Further, although the value of 10% is cited as an example of the threshold value of the difference in the maximum difference DR in the heartbeat R-R interval, the threshold value is not limited to this example, but can variously be modified. For example, the value can be 20%, or can be defined by time (ms). Further, it is also possible to adopt a configuration in which these numbers are arbitrarily changed by the user using the operation section 135.

C5. Modified Example 5

In the embodiment described above, although the pulse wave of the user is detected by the pulse wave sensor 61 of the contactless type, the method of detecting the biological information of the user is not limited to the contact type or the contactless type, but can variously be modified. For example, there can also be adopted the pulse wave sensor 61 of the contactless type of receiving the transmitted light having been transmitted through the living body instead of the pulse wave sensor 61 of receiving the reflected light. In this case, the pulse wave sensor 61 for the transmitted light is attached to the earlobe of the user to thereby detect the pulse wave of the user. Further, unlike the embodiment described above, a variation in the blood pressure can also be detected as the biological information of the user without detecting the variation in the blood flow rate. For example, a contact-type sensor for detecting the blood pressure is disposed in a portion of the image display section 20 facing the temple of the user, and thus, the variation in the blood pressure of the user is detected.

Further, although in the embodiment described above, the operation section 135 is provided to the control section 10, the configuration of the operation section 135 can variously be modified. For example, there can be adopted a configuration in which a user interface as the operation section 135 is disposed separately from the control section 10. In this case, since the operation section 135 is separated from the control section 10 provided with the power supply 130 and so on, and can therefore be miniaturized, and thus, the operability of the user is improved. Further, by providing a 9-axis sensor for detecting the motion of the operation section 135 to the operation section 135 to thereby perform a variety of operations based on the motion thus detected, the user can instinctively operate the head-mount type display device 100.

For example, it is also possible for the image light generation section to have a configuration including an organic EL (organic electroluminescence) display and an organic EL control section. Further, the image generation section, for example, can also use an LCOS (Liquid Crystal On Silicon; LCoS is a registered trademark), a digital micromirror device, and so on instead of the LCD. Further, for example, it is also possible to apply the invention to a laser retinal projection head mounted display. In the case of the laser retinal projection type, an "area to which the image light can be emitted in the image light generation section" can be defined as an image area to be recognized by the eyes of the user.

Further, for example, the head mounted display can also be formed as a head mounted display having a configuration in which each of the optical image display sections covers only a part of the eye of the user, in other words, a configuration in which each of the optical image display sections does not completely cover the eye of the user. Further, it is also possible to assume that the head mounted display is a so-called monocular head mounted display. Further, the head mounted display is not limited to the optical transmissive type, but can also be a non-transmissive type or a video transmissive type with which the user cannot visually recognize the external sight SC in a see-through manner.

Figure 17A:
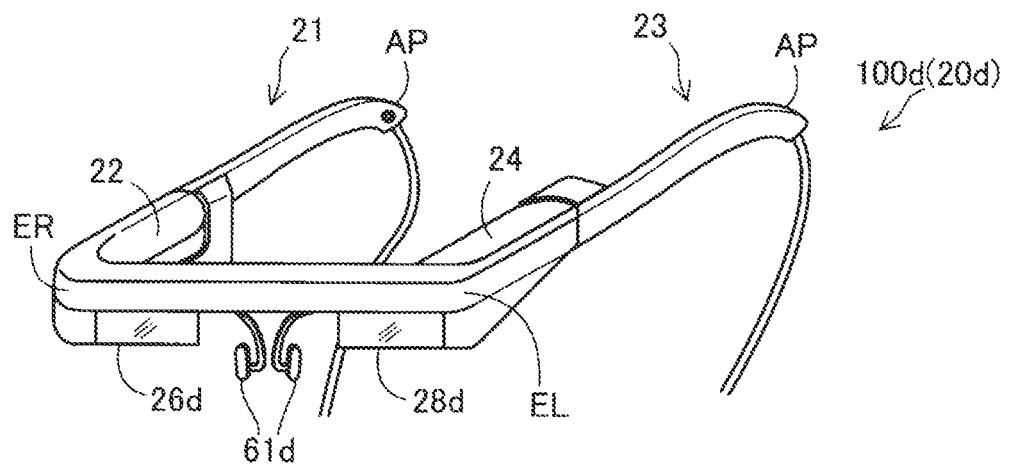
FIGS. 17A and 17B are explanatory diagrams each showing an exterior configuration of a head-mount type display device according to a modified example.
Figure 17B:
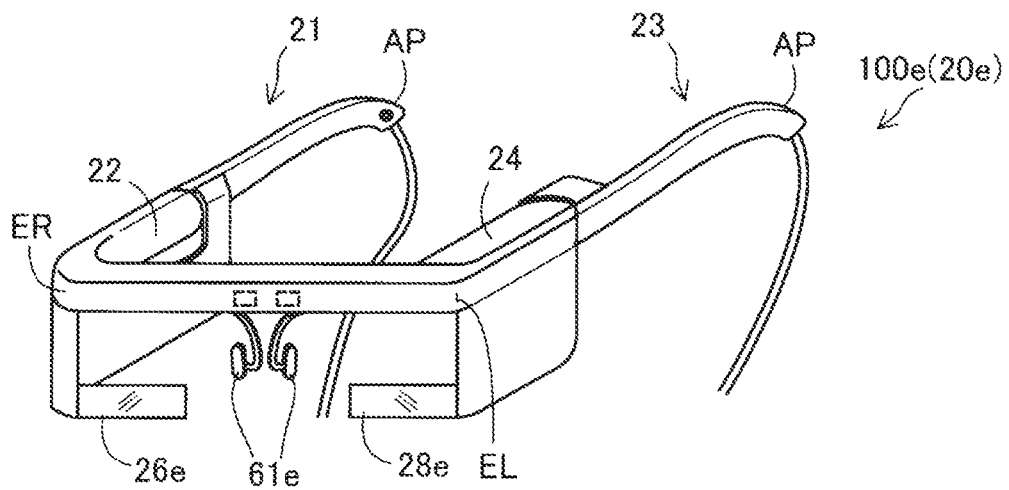

FIGS. 17A and 17B are explanatory diagrams each showing an exterior configuration of a head-mount type display device according to a modified example. In the case of the example shown in FIG. 17A, the head-mount type display device is different from the head-mount type display device 100 shown in FIG. 1 in the point that the image display section 20*d* is provided with a right optical image display section 26*d* instead of the right optical image display section 26, and the point that the left optical image display section 28*d* is provided instead of the left optical image display section 28. The right optical image display section 26*d* is formed to be smaller than the optical member of the embodiment described above, and is disposed obliquely above the right eye of the user when wearing the head-mount type display device 100*d*. Similarly, the left optical image display section 28*d* is formed to be smaller than the optical member of the embodiment described above, and is disposed obliquely above the left eye of the user when wearing the head-mount type display device 100*d*. In the case of the example shown in FIG. 17B, the head-mount type display device is different from the head-mount type display device 100 shown in FIG. 1 in the point that the image display section 20*e* is provided with a right optical image display section 26*e* instead of the right optical image display section 26, and the point that the left optical image display section 28*e* is provided instead of the left optical image display section 28. The right optical image display section 26*e* is formed to be smaller than the optical member of the embodiment described above, and is disposed obliquely below the right eye of the user when wearing the head mounted display. The left optical image display section 28*e* is formed to be smaller than the optical member of the embodiment described above, and is disposed obliquely below the left eye of the user when wearing the head mounted display. As described above, it is sufficient for each of the optical image display sections to be disposed in the vicinity of the eye of the user. Further, the size of the optical member forming the optical image display sections is determined arbitrarily, and it is possible to implement the head-mount type display device 100 having a configuration in which the optical image display sections each cover only apart of the eye of the user, in other words, the configuration in which the optical image display sections each do not completely cover the eye of the user.

Further, as the earphones, an ear hook type or a headband type can be adopted, or the earphones can be eliminated. Further, it is also possible to adopt a configuration as the head mounted display installed in a mobile object such as a vehicle or a plane. Further, it is also possible to adopt a configuration as the head mounted display incorporated in a body protector such as a helmet.

The configuration of the head-mount type display device 100 in the embodiment described above is illustrative only, and can variously be modified. For example, it is also possible to eliminate one of the direction keys 16 and the track pad 14 provided to the control section 10, or to provide another operating interface such as an operating stick in addition to or instead of the direction keys 16 and the track pad 14. Further, it is also possible to assume that the control section 10 has a configuration in which an input device such as a keyboard or a mouse is connected to the control section 10, and receives an input from the keyboard or the mouse.

Further, it is also possible to adopt an image display section of another system such as an image display section to be worn like a hat as the image display section instead of the image display section 20 to be worn like a pair of glasses. Further, the earphones 32, 34 can arbitrarily be omitted.

Further, in the embodiment described above, it is also possible to assume that the head-mount type display device 100 guides the image light beams representing the same image to the right and left eyes of the user to thereby make the user visually recognize a two-dimensional image, or to assume that the head-mount type display device 100 guides the image light beams representing respective images different from each other to the right and left eyes of the user to thereby make the user visually recognize a three-dimensional image.

Further, in the embodiment described above, it is also possible to replace a part of the configuration implemented by hardware with software, or by contraries, to replace a part of the configuration implemented by software with hardware. For example, although in the embodiment described above, it is assumed that the image processing section 160 and the sound processing section 170 are implemented by the CPU 140 retrieving and then executing the computer program, it is also possible to assume that these functional sections are implemented by hardware circuits.

Further, in the case in which a part or the whole of the function of the invention is implemented by software, the software (the computer program) can be provided in a form of being stored in a computer-readable recording medium. In the invention, the "computer-readable recording medium" is not limited to a portable recording medium such as a flexible disk and a CD-ROM, but includes an internal storage device in the computer such as a variety of types of RAM or ROM, and an external storage device fixed to the computer such as a hard disk drive.

Further, although in the embodiment described above, the control section 10 and the image display section 20 are formed as the separate constituents as shown in FIGS. 1 and 2, the configuration of the control section 10 and the image display section 20 is not limited to this configuration, but can variously be modified. For example, the configuration formed in the control section 10 can be formed inside the image display section 20 in whole or in part. Further, it is also possible to adopt a configuration in which the power supply 130 in the embodiment described above is formed alone, and can be replaced, or the configuration provided to the control section 10 can redundantly be provided to the image display section 20. For example, the CPU 140 shown in FIG. 2 can also be provided to both of the control section 10 and the image display section 20, and it is also possible to adopt a configuration in which the functions respectively performed by the CPU 140 provided to the control section 10 and the CPU provided to the image display section 20 are separated from each other.

Further, it is also possible to adopt a configuration of a wearable computer in which the control section 10 and the image display section 20 are integrated with each other, and can be attached to the clothes of the user.

C6. Modified Example 6

Although in the embodiments described above, a variety of sensors (e.g., the pulse wave sensor 61) are used for detecting the variation in the physical condition of the user, the sensors are not limited to these sensors, but can variously be modified. For example, a perspiration meter to be attached to the skin of the user and for detecting the state of perspiration of the user can also be used instead of each of the electromyographs 64, 65 of the head-mount type display device 100*f* in the second embodiment. The perspiration meter used in this modified example is a ventilated capsule perspiration meter, and measures two types of humidity, namely the air moisture content of the air before passing through the capsule, and the air moisture content of the air including the sweat after passing through the capsule, to thereby measure the perspiration amount of the user. In the case in which the perspiration amount of the user per unit time thus measured is equal to or higher than a preset threshold value, the sensor control section 165*f* determines that an abnormality exists in the physical condition of the user. In the present modified example, since the control of the display image is performed in accordance with the perspiration state of the individual user, the convenience of the user can be enhanced. It should be noted that the identification of the perspiration in the appended claims includes identification of the degree of the perspiration of the user in addition to the determination on whether or not the user is sweating.

Further, as the sensor for detecting the perspiration state of the user, a sensor other than the ventilated capsule perspiration meter can also be used. For example, in the case in which an amount of the sweat attached to the skin of the user is large, the resistance value between two electrodes measured while making the two electrodes have contact with the skin of the user is decreased, and therefore, the amount of the sweat can be identified based on the resistance value thus measured. Further, the sweat attached to the skin of the user can also be identified using a chloride ion sensor capable of detecting the chloride ions.

Although in the embodiments described above, the positions where the variety of types of sensors are mounted are explained citing the specific examples, the positions where the variety of types of sensors are mounted can variously be modified. For example, the ear thermometer 66 for measuring the body temperature of the user can also be mounted on the left ear of the user. Further, in order to measure the body temperature of the user, a thermometer to be held in the armpit to measure the body temperature can also be used as a thermometer other than the ear thermometer 66.

Further, although the eye imaging cameras 37*f*, 38*f* are used for determining the redness of the eyes, the state of the redness of the eyes of the user can also be identified by using near-infrared LEDs. Since hemoglobin included in blood absorbs the near-infrared ray, by irradiating the eyes with the near-infrared ray to detect the reflected light, the state of the redness of the eyes of the user can be identified. Further, since the reflectance is different between the black part and the white part of the eye of the user, by irradiating the eyes with the near-infrared ray, the size of the pupil can be identified. Further, although in the second embodiment described above, the taken-image processing section 166 binarizes the taken images of the eyes of the user, the binarization is not necessarily required, but it is also possible to identify the proportion of the red pixels based on the R, G, and B components.

Further, by measuring the reflectance from the reflected light of the near-infrared ray applied to the eyes of the user, the moisture state of the surface of the eyes is determined, and thus, the degree of the dry eye can also be identified. Further, in the second embodiment, the sensor control section 165*f* performs the pattern matching with the eyes in the predetermined dry eye condition based on the images of the eyes of the user taken by the eye imaging cameras 37*f*, 38*f* to thereby also identify the degree of the dry eye. Further, it is also possible to close the eyes and then open the eyes to thereby previously set the time (break up time) until a tear film is broken, and then make the user visually recognize the caution message based on the interval between the blinks.

Although in the second embodiment described above, the abnormality of the physical condition of the user is determined based on the variation with respect to the average temperature in a certain period from the beginning of the acquisition of the body temperature of the user as in the case with, for example, an abnormality of the body temperature in which the body temperature rises to be higher than the reference body temperature or drops to be lower than the reference body temperature, the determination method of the abnormality of the physical condition of the user is not limited to this method, but can variously be modified. For example, in the case in which the temperature lower than 35 degree or equal to or higher than 38 degree is measured as the body temperature of the user, the sensor control section 165f can also determine that an abnormality exists in the physical condition of the user. Further, these threshold temperatures can arbitrarily be set by the user. Further, regarding the determination of the redness of the eyes of the user, the proportion of the number of the red pixels in the data of the individual user can previously be set as the threshold value, or it is also possible to adopt a configuration in which the caution message is different in accordance with the proportion of the number of the red pixels.

Further, although in the display control process of the second embodiment described above, the caution message is displayed in the case in which the abnormality is detected with respect to one of the criteria of the plurality of pieces of biological information, it is also possible to perform the display control process in accordance with combinations of the abnormalities in the plurality of pieces of biological information.

Although in the second embodiment described above, the voltage values varying in accordance with the expansion and contraction of the external ocular muscle and the internal ocular muscle of the eyes of the user are detected by the electromyographs 64, 65, it is also possible for the sensor control section 165f to perform the control based on the expansion and contraction of either one of the external ocular muscle and the internal ocular muscle.

Although in the embodiments described above, the pulse wave sensor 61, the electromyographs 64, 65, and so on for detecting the biological information of the user are connected to the image display section 20 of the head-mount type display device 100 in a wired manner, the communication method of the biological information between the detection section and the head-mount type display device 100 can variously be modified. For example, the biological information can also be communicated wirelessly between the detection section and the head-mount type display device 100. As the method of wirelessly communicating the biological information, there can be cited, for example, methods using Bluetooth (registered trademark), a wireless local area network (LAN), and near field communication (NFC).

Although in the embodiments described above, the earphones 32, 34 output the sounds, the method of making the user recognize the sound information is not limited to this configuration, but can variously be modified. For example, the sounds can be output by a speaker, or it is also possible to make the user recognize the sound information using a vibration of bone conduction. Further, regarding the warning sounds or the like, the warning can be given to the user using a vibration.

Although in the second embodiment described above, the ear thermometer 66 measures the body temperature of the user, the device for measuring the body temperature of the user can variously be modified. For example, it is possible for a radiation thermometer to measure the intensity of the infrared ray or the visible light beam radiated from the user to thereby measure the body temperature of the user. The radiation thermometer can measure the body temperature of the user without having contact with the user, and therefore does not necessarily need to have contact with the user, and is convenient.

Further, although in the embodiments described above, the pulse wave sensor 61 and the electromyographs 64, 65 are used as the detection section for the biological information of the user, the detection section for the biological information of the user is not limited to these devices, but can variously be modified. For example, the detection section can also be a pedometer (a manpo-kei (a registered trademark)) for measuring the walk count of the user, or an activity meter for measuring the calorie consumption in a variety of activities such as walking or a desk work of the user in one day in addition to the walk count. Further, the detection section can also be a sleep meter for detecting turning over or a movement of the chest of the user during sleep to thereby identify the state of the user during sleep.

The invention is not limited to the embodiments and the modified examples described above, but can be implemented with a variety of configurations within the scope or the spirit of the invention. For example, the technical features in the embodiments and the modified examples corresponding to the technical features in the aspects described in SUMMARY section can arbitrarily be replaced or combined in order to solve all or apart of the problems described above, or in order to achieve all or apart of the advantages described above. Further, the technical feature can arbitrarily be eliminated unless described in the specification as an essential element.

The entire disclosure of Japanese Patent Application Nos. 2013-136054, filed Jun. 28, 2013 and 2014-053187, filed Mar. 17, 2014 are expressly incorporated by reference herein.

What is claimed is:

1. A head-mount type display device comprising:
an image display device adapted to allow a user to view an image when mounted on a head of the user;
a detection section adapted to
   detect biological information of the user in response to the image display device beginning to allow the user to view the image, the biological information comprising information for identifying a pulse wave,
   calculate a reference value based on the biological information detected by the detection section during an initial use time period, the initial use time period comprising a predetermined time period that begins when the detection section begins detecting the biological information in response to the image display device beginning to allow the user to view the image,
   calculate another value based on the biological information detected by the detection section during another time period after the initial use time period, and
   determine whether the another value varies from the reference value by more than a predetermined threshold value; and
an annunciation section adapted to
   inform the user of image control information in response to a determination that the another value varies from the reference value by more than the predetermined threshold value, the image control information comprising a predetermined message configured to prompt the user to stop viewing the image using the image display device of the head-mount type display device,
wherein
   each of the reference value and the another value is a value of a maximum difference in a heartbeat interval, the value of the maximum difference in the heartbeat interval is a difference between a maximum value of the heartbeat interval and a minimum value of the heartbeat interval in a predetermined number of beats of the heart, and the image display device displays the predetermined message after the image is displayed on the image display device.

2. The head-mount type display device according to claim 1, wherein the detection section is disposed so as to have contact with the user, and keep the contact with the user.

3. The head-mount type display device according to claim 1, wherein the annunciation section allows the user to view the image control information using the image display device.

4. The head-mount type display device according to claim 1, wherein the annunciation section outputs the image control information as a sound.

5. The head-mount type display device according to claim 1, wherein the annunciation section is further adapted to perform control of changing the image so as not to be viewable by the user.

6. A method of controlling a head-mount type display device including an image display device adapted to allow a user to view an image when mounted on a head of the user and a detection section adapted to detect biological information of the user, the method comprising:

detecting the biological information in response to the image display device beginning to allow the user to view the image;

calculating a reference value based on the biological information detected during an initial use time period, the initial use time period comprising a predetermined time period that begins when the detecting of the biological information in response to the image display device beginning to allow the user to view the image begins;

calculating another value based on the biological information detected during another time period after the initial use period;

determining whether the another value varies from the reference value by more than a predetermined threshold value; and informing the user of image control information in response to a determination that the another value varies from the reference value by more than the predetermined threshold value, wherein the biological information comprises information for identifying a pulse wave, each of the reference value and the another value is a value of a maximum difference in a heartbeat interval, the value of the maximum difference in the heartbeat interval is a difference between a maximum value of the heartbeat interval and a minimum value of the heartbeat interval in a predetermined number of beats of the heart, the image control information comprises a predetermined message configured to prompt the user to stop viewing the image using the image display device of the head-mount type display device, and the image display device displays the predetermined message after the image is displayed on the image display device.

7. The head-mount type display device according to claim 1, wherein the image control information is further configured to notify the user that the image will be changed so as not to be viewable by the user.

8. The head-mount type display device according to claim 1, wherein the annunciation section is further adapted to change the image so as not to be viewable by the user if the another value varies from the reference value by more than the predetermined threshold value for a predetermined amount of time after the annunciation section informs the user of the image control information.

9. The head-mount type display device according to claim 1, wherein the detection section is adapted to detect the biological information of the user at periodic intervals.

10. The head-mount type display device according to claim 1, wherein the detection section comprises a pulse wave sensor, and the pulse wave sensor is configured to identify the pulse wave from a side of the head of the user.

* * * * *